US009653002B2

(12) United States Patent
Alberts et al.

(10) Patent No.: US 9,653,002 B2
(45) Date of Patent: May 16, 2017

(54) SYSTEM AND METHOD FOR MOTOR AND COGNITIVE ANALYSIS

(75) Inventors: Jay L. Alberts, Chagrin Halls, OH (US); Cameron C. McIntyre, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1138 days.

(21) Appl. No.: 13/510,683

(22) PCT Filed: Nov. 19, 2010

(86) PCT No.: PCT/US2010/057453
§ 371 (c)(1),
(2), (4) Date: Sep. 7, 2012

(87) PCT Pub. No.: WO2011/063248
PCT Pub. Date: May 26, 2011

(65) Prior Publication Data
US 2012/0330182 A1    Dec. 27, 2012

Related U.S. Application Data

(60) Provisional application No. 61/262,662, filed on Nov. 19, 2009.

(51) Int. Cl.
*A61B 5/103*    (2006.01)
*G09B 23/28*    (2006.01)
(Continued)

(52) U.S. Cl.
CPC .............. *G09B 23/28* (2013.01); *A61B 5/162* (2013.01); *A61B 5/4082* (2013.01); *A61B 5/4833* (2013.01); *A61B 5/4836* (2013.01)

(58) Field of Classification Search
CPC ..... A61B 3/024; A61B 5/168; G06F 19/3431; G06F 19/3443
(Continued)

(56) References Cited

U.S. PATENT DOCUMENTS 5,565,949 A * 10/1996 Kasha, Jr. .............. A61B 3/024
                                                    351/224
5,911,687 A *  6/1999 Sato ...................... G06F 19/322
                                                    600/300
(Continued)

FOREIGN PATENT DOCUMENTS

JP    WO 2009028221 A1 *  3/2009  ........... A61B 5/0488

OTHER PUBLICATIONS

United States Patent and Trademark Office, International Search Report in International Application No. PCT/US10/57453, dated Jan. 11, 2011.

*Primary Examiner* — Max N Hindenburg
*Assistant Examiner* — Jonathan M Foreman
(74) *Attorney, Agent, or Firm* — Lowe Graham Jones PLLC; Bruce E. Black

(57) ABSTRACT

A cognitive and/or motor skill testing system and method may include a processor that records respective time information for each of multiple positions of a display device that are traced during administration of a test, that determines speed and/or velocity values based on the recorded time information, and that outputs test result information based on the determined values. The test result information may be based on a comparison between a graphed curve of such values to an ideal curve. The positions may correspond to a path between displayed targets whose size and/or distance therebetween depend on past test performance. The system and/or method may output a change expected with a change to therapy parameters for a patient, where the expected change is determined based on changes which occurred in other patients having similar test results and therapy parameters as those of the patient.

20 Claims, 25 Drawing Sheets

(51) Int. Cl.
*A61B 5/00* (2006.01)
*A61B 5/16* (2006.01)

(58) Field of Classification Search
USPC .......................................... 600/300, 558, 595
See application file for complete search history.

(56) References Cited

U.S. PATENT DOCUMENTS

| | | |
|---|---|---|
| 6,435,878 B1 | 8/2002 | Reynolds et al. |
| 6,517,480 B1 | 2/2003 | Krass |
| 7,211,050 B1* | 5/2007 | Caplygin ............... A61B 5/168 |
| | | 351/222 |
| 7,294,107 B2 | 11/2007 | Simon et al. |
| 2007/0162235 A1 | 7/2007 | Zhan et al. |
| 2008/0133141 A1 | 6/2008 | Frost |
| 2008/0242950 A1 | 10/2008 | Jung et al. |
| 2009/0198354 A1 | 8/2009 | Wilson |
| 2009/0242399 A1 | 10/2009 | Kamath et al. |
| 2011/0137196 A1* | 6/2011 | Kakei .................. A61B 5/0488 |
| | | 600/546 |

* cited by examiner

INSTRUCTIONS

ON THE NEXT SCREEN, YOU WILL SEE THREE CIRCLES NUMBERED 1 THROUGH 3.

MOVE YOUR MOUSE TO CIRCLE NUMBER 1 (YOU DO NOT NEED TO "CLICK" ON THE CIRCLE).

WHEN YOU DO THIS, THE TEST WILL AUTOMATICALLY BEGIN.

MOVE YOUR MOUSE IN NUMERICAL ORDER, 1,2,3 JUST LIKE A "CONNECT THE DOTS" DRAWING, MAKING SURE YOU ENTER THE MIDDLE OF THE CIRCLE.

EACH TIME YOU ENTER A CIRCLE, THE CIRCLE WILL TURN GREY TO SHOW THAT YOU HAVE HIT THE CIRCLE.

IF THE CIRCLE DOES NOT TURN GREY, IT MEANS THAT YOU DID NOT ENTER THE CIRCLE COMPLETELY, OR YOU WENT IN THE WRONG ORDER.

IF THIS HAPPENS, FIND THE CIRCLE YOU ARE LOOKING FOR, AND DRAW TO IT NOW.

WHEN YOU HIT THE LAST CIRCLE, THE TEST WILL BE OVER.

YOU WILL COMPLETE THIS TASK FIVE TIMES, AND AFTER THE FINAL TIME, THE COMPUTER WILL TELL YOU THAT THE TASK IS COMPLETED.

[START THE TEST]

FIG. 8

INSTRUCTIONS

THIS NEXT TASK IS A LITTLE DIFFERENT.

YOU WILL SEE A CIRCLE WITH A LETTER A ON IT, SURROUNDED BY OTHER CIRCLES WITH Bs ON THEM.

THE A CIRCLE IN THE CENTER WILL SERVE AS "HOME BASE", AND YOU WILL BRING YOUR MOUSE BACK INTO IT, AND OUT OF IT TOWARDS WHICHEVER B CIRCLE IS LIGHTING UP.

YOU WILL ALWAYS MOVE YOUR MOUSE TO THE CIRCLE THAT IS LIGHTING IN GREEN FOR THIS TASK.

THE ORDER IN WHICH THE CIRCLES LABELED B LIGHT UP IS RANDOM.

EACH CIRCLE LABELED B WILL LIGHT UP TWICE.

YOU WILL COMPLETE THIS TASK 5 TIMES BEFORE THE COMPUTER TELLS YOU THAT YOU HAVE FINISHED.

[START THE TEST]

FIG. 11

INSTRUCTIONS

THIS NEXT TASK IS VERY SIMILAR TO THE ONE YOU JUST COMPLETED, BUT THERE WILL BE MORE NUMBERS.

YOU WILL SEE CIRCLES NUMBERED FROM 1 TO 25.

MOVE YOUR MOUSE TO CIRCLE NUMBER 1, AND THE TEST WILL AUTOMATICALLY BEGIN (JUST AS BEFORE).

FROM HERE, MOVE THE MOUSE TO THE NEXT NUMBER IN THE SERIES, ALL THE WAY UP TO NUMBER 25.

THIS TIME, THE CIRCLES WILL NOT GREY WHEN YOU HIT THEM.

YOU NEED TO MAKE SURE THAT YOU ARE GOING IN THE CORRECT ORDER BECAUSE YOU HAVE NO INDICATION OF IF YOU HIT THE RIGHT TARGET OR NOT.

ONCE YOU ENTER THE CIRCLE NUMBER 25, THE TEST WILL BE OVER.

YOU WILL ONLY TAKE THIS TEST ONCE.

[START THE TEST]

FIG. 14

INSTRUCTIONS

THIS NEXT TASK WILL HAVE BOTH NUMBERS AND LETTERS ON IT.

YOU WILL BE ASKED TO SWITCH BACK AND FORTH BETWEEN WHICH NUMBER CORRESPONDS TO WHICH LETTER OF THE ALPHABET.

FOR EXAMPLE, 1 GOES TO A, 2 TO B, 3 TO C, AND SO FORTH.

YOU WILL CONTINUE GOING THROUGH THE SERIES, FROM NUMBER TO LETTER UNTIL YOU REACH THE LAST NUMBER.

LIKE THE LAST TEST, THE CIRCLES WILL NOT GREY WHEN YOU HIT THEM.

YOU NEED TO MAKE SURE THAT YOU ARE GOING IN THE CORRECT ORDER BECAUSE YOU HAVE NO INDICATION OF IF YOU HIT THE RIGHT TARGET OR NOT.

ONCE YOU ENTER THE LAST CIRCLE, THE TEST WILL BE OVER.

THIS TEST WILL ALSO ONLY BE TAKEN ONCE.

START THE TEST

FIG. 17

SYSTEM AND METHOD FOR MOTOR AND COGNITIVE ANALYSIS

CROSS-REFERENCE TO RELATED APPLICATIONS

This application is a 371 national phase application of International Application No. PCT/US10/57453, filed Nov. 19, 2010, which claims the benefit, under 35 U.S.C. §119(e), of U.S. Provisional Patent Application No. 61/262,662, filed Nov. 19, 2009, the contents of both of which is are hereby incorporated by reference in its entirety their entireties.

TECHNICAL FIELD

Inventions described herein relate generally to a system and method to objectively qualitatively quantify cognitive, motor, and cognitive-motor functioning.

BACKGROUND

There are various neuromotor and neurocognitive disorders including Alzheimer's disease, Parkinson's Disease (PD), and progressive supranuclear palsy to name a few. Neuromotor and neurocognitive disorders affect motor function, cognitive function or both.

In order to properly treat many neuromotor and neurocognitive disorders, it is desirable to better understand or classify an individual's condition. Accordingly, a variety of tests have been developed for various types of diseases. For example, one scale for assessing a patient's Parkinson's disease is the Unified Parkinson's Disease Rating Schedule (UPDRS). Various other tests exist that are utilized by a clinician to help the clinician categorize a patient's disorder.

To more efficiently administer and objectively analyze results of such tests, computerized systems for administering some of such tests have been proposed. U.S. Pat. No. 6,435,878 ("the '878 patent") proposes a system where a user's reaction time to a stimulus can be measured. However, the proposed system does not measure the quality of the user's interaction with the system. The system of the '878 patent also dynamically modifies a presentation time or quantity of a stimulus for the stimulus based on the user's performance, but does not qualitatively modify test difficulty based on user performance.

U.S. Pat. No. 7,294,107 ("the '107 patent") similarly refers to a testing system with which user reaction time can be measured. However, as with the '878 patent, the system does not measure the quality of the user's interaction with the system. The system of the '107 patent also determines based on user performance which tests to administer and whether to terminate a test, but does not qualitatively modify a particular test's difficulty based on user performance.

U.S. Pat. No. 6,517,480 ("the '480 patent") refers to a testing system in which a maze trace is detected and an overall time for completion of the test is detected, but the system does not provide for any qualitative measurement of the user's performance of the test or for modifying testing difficulty in view of user performance.

Moreover, none of the '878, '107, and '480 patents provide a system or method for time-based testing of a degree of cognitive ability, nor do they provide a system or method that presents data regarding a correlation of test results to patient information, such as medications the patient is taking and/or stimulation parameters used for Deep Brain Stimulation (DBS) of the patient.

SUMMARY

This invention relates to systems and methods for the objective qualitative and quantitative measurement of cognitive, motor and/or cognitive-motor function of a patient. Cognitive tests may include, for example, one or more of a trail making test, Kaplan Baycrest Neurocognitive Assessment test, a Mini Mental State Exam, and Raven's Progressive Matrices test. This invention also relates to systems and methods for outputting expected changes to test results caused by changes in the patient's environment, where the output is based on past test performances. This invention also relates to systems and methods for dynamic qualitative modification of an administered test based on test performance.

Example embodiments of the present invention provide a system and method that qualitatively measure a user's movements when taking a computerized test, by recording time information for each of a plurality of positions between start and end positions, which positions correspond to a path of the user's movement between the start and end test positions when taking the test, and automatically analyzing such information. In particular, the inventors have discovered that it is advantageous to sample positional and associated time information at a rate that is double that of typical Malian movement. Specifically, in an example embodiment of the present invention, the positional and associated time information is sampled at a rate of 30 Hz.

Example embodiments of the present invention provide for determining speed and/or acceleration information regarding user movement during and provide a computer-administered test. In an example embodiment, the system and method further analyzes a quality of the speed and/or acceleration, for example, based on a degree of smoothness and/or shape of a curve representing change of the speed and/or acceleration over the time period in which the test was taken.

In one example embodiment, the system provides a testing system that tracks patient-controlled movement, such as by storing time and position information responsive to movement of a pointer device (e.g., a mouse or stylus or a touch screen that responds to a user's touch) performed by a user. The stored time and position information can be evaluated (e.g., at a server) using a combination of movement analysis techniques to provide corresponding kinematic data and other data representative of the patient-controlled movement. The test can be designed to capture data reflecting cognitive and motor functions of the user individually anchor concurrently. The resulting data thus can be utilized to characterize and classify movement patterns for a variety of purposes, including: diagnosing a movement disorder; evaluating a current treatment paradigm; tracking progression of a movement disorder; providing rehabilitative intervention; and optimizing or tuning an intervention.

As a further example, the results can be part of a closed bop system to tune stimulation parameters for DBS, such as by providing an interface between the local computer where the test is performed and a programmable implantable stimulator, which may be manually or automatically manipulated based on analysis results of the administered test(s).

Specifically, a system and method of the present invention may provide information regarding how changes to patient treatment parameters have affected test results of other patients who have been determined to have similar characteristics of a present patient based on similarities of past test results.

To facilitate use and access, the test can be implemented as an Internet-based application that can be accessed by an authorized user at a remote location via a predetermined resource locator (e.g., a URL). Additionally, by implementing the system as a web-based application, test data can be maintained (anonymously) for a plurality of patients at a central server to facilitate further analysis and research. For example, results of the testing for a plurality of users further can be aggregated to generate a new index for classifying movement disorders or determining the severity of a movement disorder, which may (or may not) be correlated with existing standards, such as the commonly used Unified Parkinson's Disease Rating Scale (UPDRS). For example, a composite score maybe calculated that combines both cognitive performance (e.g., related to dwell time or set switching time, where set switching time refers to the time taken to refocus attention from one task to another) and motor performance (e.g., related to straightness of movement), which composite score may be useful for simultaneous assessment of both cognitive and motor function. Since the measure would be captured in a standard manner across users, the measure may be used to characterize a current user's performance against a larger group of patients. The clinician may use the comparative data to explore effects of various medical interventions and their predicted outcomes.

According to an example embodiment of the present invention, a computer-implemented testing method may include: recording, by a processor, respective time information for each of a plurality of positions of a display device that are traced during administration of a test; determining, by the processor, a plurality of speed values and/or a plurality of velocity values based on the recorded time information; and outputting, by the processor, test result information based on the speed and/or velocity values.

In an example method, the output information includes a score computed based on the determined plurality of speed and/or velocity values.

The method may further include plotting the values as a graph curve, and comparing at least one slope of the curve to at least one slope of a stored curve. The score maybe based on the comparison.

The method may include determining derivatives of the velocity values, and the test result information may be based additionally on the derivatives. For example, the derivatives may include acceleration values.

The method may include generating at least a portion of the test result information by calculating an average, standard deviation, mean square error, and/or root mean square error of a difference of (a) the determined values from ideal values, or (b) derivative values of the determined values from ideal derivative values.

The method may include, responsive to the trace of the plurality of positions, recording the plurality of traced positions. Each of the determined values may be recorded in association with respective ones of the recorded plurality of traced positions.

According to an example, the recorded plurality of traced positions are recorded at a rate of approximately 30 Hz.

According to an example, the output information includes a graph that plots the determined values against the recorded plurality of traced positions.

According to an example, each of the plurality of traced positions is recorded as a respective pair of an abscissa value and an ordinate value. For each pair of abscissa and ordinate values, the abscissa and ordinate values are separately associated with respective ones of the determined values.

In an example method, the output information indicates cognitive ability and/or motor skill of a user in response to whose movement the plurality of positions are traced.

In an example method, the display device is part of a patient terminal, the time information is recorded at a server coupled to the patient terminal via a network, and the test result information is output at a clinician terminal coupled to the server via the network. In an example embodiment, the network includes the Internet.

According to an example embodiment of the present invention, a computer-implemented testing method may include: displaying in a display device a first target and a second target; responsive to user input corresponding to a trace of a plurality of positions in the display device, which, in combination, form a path from the first target to the second target, recording, by a processor, respective time information for each of the plurality of positions; and determining, by the processor, and outputting, information regarding a cognitive ability and/or a motor skill of a user based on the recorded time information.

The method may further include, in accordance with at least a portion of the determined information, modifying a size of the targets and/or a distance between the targets.

Alternatively or additionally, the method may further include, in accordance with the determined information, setting (a) a size of and/or (b) a distance between a pair of, additional displayed targets.

According to an example embodiment dine present invention, a computer-implemented testing method may include: displaying in a display device a first target and a second target; responsive to user input corresponding to a path between the first and second targets, determining, by a processor, a cognitive ability and/or a motor skill; and, in accordance with the determined ability and/or skill, (I) modifying, by the processor, a size of the targets and/or a distance between the targets; and/or (II) setting, by the processor, (a) a size of, and/or (b) a distance between a pair of additional displayed targets.

According to an example embodiment of the present invention, a computer-implemented testing method may include: in accordance with a test-performance history of a user, selecting, by a processor, (a) a size of, and/or (b) a distance between, targets of a testing user interface; and displaying in a display device the testing user interface including the targets, in accordance with the selected size and/or distance.

According to an example embodiment of the present invention, a computer-implemented method for providing testing information may include: recording, by a processor, a first at least one therapy parameter applied to a patient; recording, by the processor, a first test result for the patient in association with the first at least one therapy parameter; and, for a user-input proposed change to the at least one therapy parameter to obtain a changed at least one therapy parameter: searching, by the processor, for a set of at least one patient for each of whom (a) the first test result or a respective second rest result that deviates from the first test result by less than a threshold amount is recorded in association with the first at least one therapy parameter or a second at least one therapy parameter that deviates from the first at least one therapy parameter by less than a predetermined threshold amount, and (b) a respective test result is recorded in association with the changed at least one therapy parameter or another respective at least one therapy parameter that deviates from the changed at least one therapy parameter by less than a predetermined threshold amount; and outputting, by the processor, information (a) indicative of an expected change to the first test result in response to the proposed change to the at least one therapy parameter, and (b) based on the at least one respective test result recorded for the set of at least one patient in association with the changed at least one therapy parameter or another respective at least one therapy parameter.

In an example, the output information includes the expected changed test result.

In an example, the output information includes an expected medical condition classification.

In an example, the output information includes an expected change in a medical condition classification.

According to an example embodiment of the present invention, a computer-implemented method for providing testing information may include: recording a set of at least one therapy parameter applied to a patient; recording a result of a test taken by the patient, the recordation being in association with the at least one therapy parameter; and, for a user input proposed change to the at least one therapy parameter, outputting an expected change to the test result for a repeated performance of the test by the patient, based an changes to test results of other patients in response to recorded changes to respective sets of at least one parameter applied to the other patients.

According to an example embodiment of the present invention, a system for analyzing motor and cognitive functions of a patient may include: a display device for providing a graphical user interface (GUI); and at least one processor configured to: present an arrangement of graphical targets on the GUI; generate test data responsive to user-controlled movement relative to the arrangement of graphical interactive targets; and, based on the test data, compute analysis data including velocity data, acceleration data, speed data, tangential acceleration data, and/or, for a deviation of one or more lines formed by the movement to one or more respective ideal lines, an average, a mean square error, and/or a root mean square error for the deviation.

In an example embodiment, the test data includes position data representing a plurality of positions corresponding to the movement and temporal information associated with the plurality of positions.

In an example embodiment, the at least one processor is configured to compute a respective dwell time for each of at least one of the graphical targets.

In an example embodiment, the processor is configured to: provide a plurality of different tests during respective test intervals, respective analysis data computed for each of the tests; and output an indication of motor and/or cognitive function collectively based on the analysis data computed for the plurality of different tests. In an example embodiment, the plurality of different tests includes at least two of a sevens test, a trail making test, a clock drawing test, a reaction time and subsequent movement task test, a center-out test, an Archimedes spiral test, a judgment of line orientation test, and tests whose complete renderings are dynamically provided as the user takes the tests.

In an example embodiment, the at least one processor is configured to generate a patient GUI, a management GUI, and a research GUI depending on an assigned user-authorization level.

The various methods and system components described herein may be practiced and provided, each alone, or in various combinations.

An example embodiment of the present invention is directed to one or more processors, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The one or more processors may be embodied in a server or user terminal(s) or combination thereof. The user terminal may be embodied, for example, as a desktop, laptop, hand-held device, Personal Digital Assistant (PDA), television set-top Internet appliance, mobile telephone, smart phone, etc., or as a combination of one or more thereof. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein, and/or for storing output data produced via execution of the methods described herein.

An example embodiment of the present invention is directed to a method, e.g., of a hardware component or machine, of transmitting instructions executable by a processor to perform the methods described herein.

BRIEF DESCRIPTION OF THE DRAWINGS

FIG. 8 depict a screen shot GUI that can be utilized for providing instructions for a "seven's test", according to an example embodiment of the present invention.

FIG. 11 depicts a screen shot GUI that can be utilized for providing instructions for a reaction test, according to an example embodiment of the present invention.

FIG. 14 depicts a screen shot GUI that can be utilized for providing instructions for a computer-implemented trail making test (Part A), according to an example embodiment of the present invention.

FIG. 17 depicts a screen shot GUI that can be for providing instructions for a computer-implemented trail making test (Part B), according to an example embodiment of the present invention.

DETAILED DESCRIPTION

Figure 1:
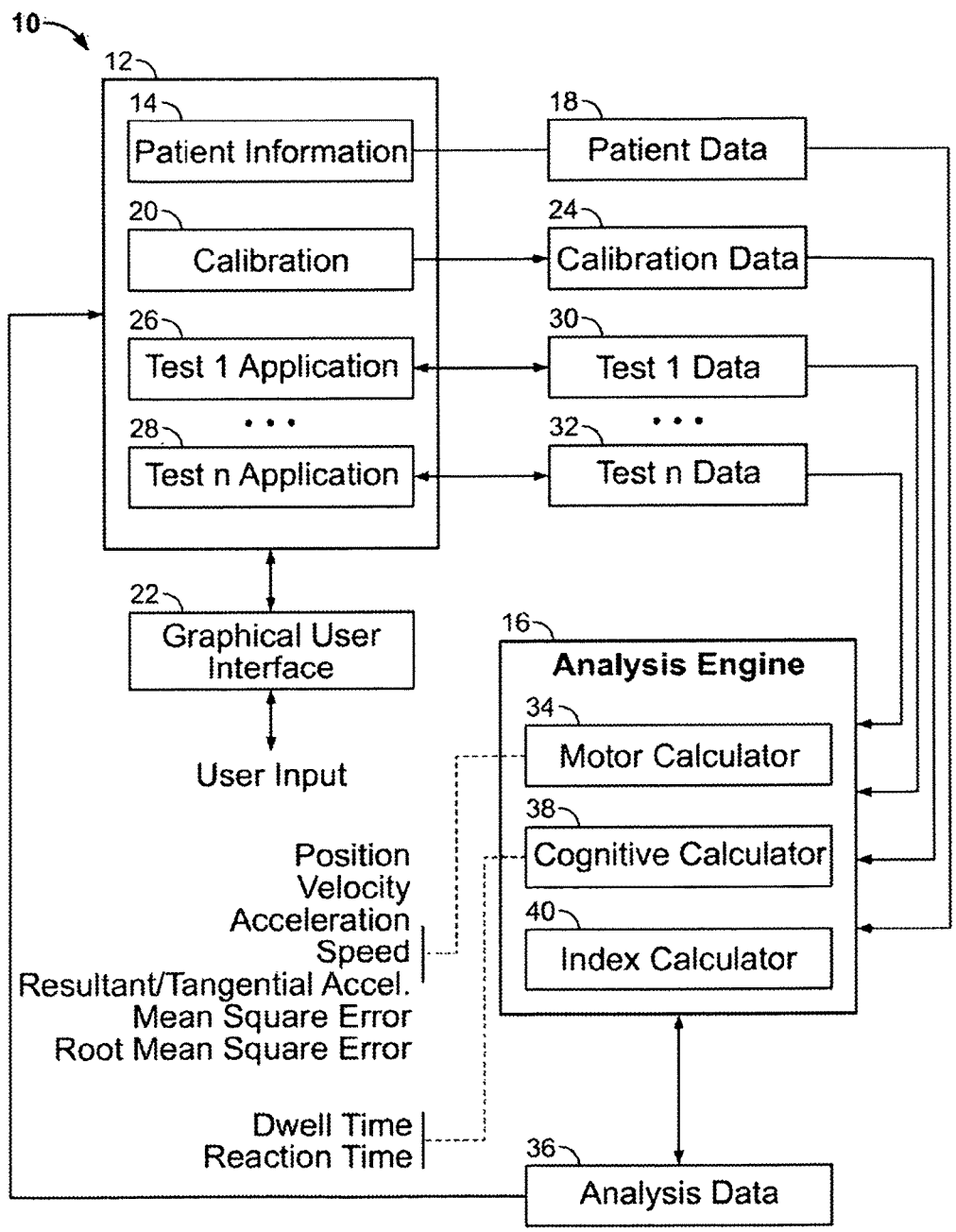
FIG. 1 is a block diagram of a test and analysis system, according to an example embodiment of the present invention.

FIG. 1 depicts an example of a test system 10 that can be implemented according to an aspect of the invention. The system 10 includes a test engine 12 that includes methods and functions that are utilized to acquire data relevant to the testing process performed by the system 10. In an example embodiment, the test engine 12 may be located at a server to which a user computing device may connect to remotely access the methods and functions of the test engine 12.

The test engine 12, for example, can include a patient information module 14. The patient information module 14 can be programmed to acquire patient information that can be provided to an analysis engine 16 in the form of patient data 18. The patient information can include a series of templates or forms (e.g., an XML or other document) that can be completed by a user using an appropriate user input device, such as a keyboard and/or mouse and/or stylus. Examples of patient information include log-in information to authenticate the user with the system, such as a log-in ID and password. The patient information can also include information about a patient's current health condition as well as information about the environment in which the patient is taking the test. Additional information can be acquired relating to medication that the patient is currently taking, including names of medication, dosage, number of times per day, and the time since the last dosage. Those skilled in the art will appreciate various types of forms and constructs that can be utilized to acquire and send the patient data 18 to the analysis engine 16.

The test engine 12 also includes a calibration module 20 that is programmed to calibrate the system such as for remote operation in which specifics of the users' test equipment may be unknown. The calibration component 20, for example can be utilized to ascertain a relative two-dimensional size of a display or monitor on which the test is being implemented. For example, a graded scale can be graphically rendered onto a display, such as a series of spaced apart lines that are provided with a corresponding normalized scale known to the programmer. An article can be provided to the user of a known size (e.g., an 8½"×11" sheet of paper, a dollar bill, or credit card), which can be positioned adjacent to the scale by the user to ascertain dimensions (e.g., in both the x and y directions) of the user's display according to size of the image being displayed to the user via the graphical user interface 22. A user can in turn enter the corresponding score into the system 10 as calibration data 24 that is utilized by the analysis engine 16. Thus, by knowing the relative display size for the user's computing device; appropriate geometry and position information can be obtained from the subsequent battery of tests to be performed. The analysis engine 16 can employ the calibration data 24 to scale the corresponding testing data consistent with the user's particular test environment (e.g., display screen) on which the user is taking the test. Specifically, the data presented to the user for the test and/or the test results may be scaled according to the calibration data. For example, accuracy (i.e., size) of displayed targets and/or distances between displayed targets may be modified according to Fitts' law in accordance with the user's test environment.

In an alternative example embodiment of the present invention, the calibration may be performed by transmitting data for presentation of three or four targets in the user's screen, one target at each corner of the screen. The system may record a number of pixels or defined X, Y positions between the targets as a representation of vertical and horizontal distances between the targets, which distances may be used as calibration data for scaling test data.

Alternatively or additionally, certain patient devices can be pre-configured having known configurations, such that calibration may be omitted. For example, devices having a predetermined configuration may be registered with the system. For instance, such preregistered devices or terminals can reside at doctors' offices, at hospitals, or other institutions.

In an alternative example embodiment, differences in the display screens may be ignored, and the test data presented to the user and the test result may be uniform across the various test platforms.

The test engine 12 also includes a plurality of test applications (e.g., functions or methods) 26 and 28, indicated as TEST I application through TEST N application, where N is a positive integer denoting any number of tests. Each test application can be programmed in a manner to test motor and/or cognitive functions, and/or a combination of motor and cognitive functions, of a user.

For example, the test can be similar to known tests such as a "Seven's test" (described in detail below with respect to FIGS. 9 and 10), a trail making test such as the trail making test parts A and B, a clock drawing test, and a reaction-time and motor task that can be utilized to test appropriate motor and/or neurocognitive functions of the user. Other tests with which the test engine 12 maybe programmed may include a center-out test (which assesses information processing speed (e.g., deciding to which target to move) and motor performance (e.g., quality of movement to a given target)), an Archimedes spiral test (to assess tremor in Parkinson's patients, where, as the patient progresses outward, tremor intends to increase), Benton's judgment of line orientation test (which measures visuospatial judgment in brain-injured patients), and tests whose complete renderings are dynamically provided as the user takes the tests. For example, a cyclical tracking test may be provided, for which a pattern for the user to trace is provided that includes points rendered after the user begins to trace the pattern. For example, a sine wave, circle, or other pattern, which changes or moves as the user traces the pattern may be displayed.

Each test application 26 to 28 can be provided to a user computer in an interactive manner that provides interactive graphical objects in the GUI 22, within a hardware display device, such as a computer or tablet screen. Such interactivity can be implemented through the use of an action script or other functions or methods that can be provided to the user, some of which can vary according to the platform in which the test engine 12 is being implemented, for example, based on a calibration as described above.

In an example embodiment, the test engine 12 can be implemented using the Flash platform, such as can be programmed using. ADOBE® FLEX®software available from Adobe Systems Incorporated. The Flash platform has advantages in that, tot example, it has an extremely high market penetration and no additional software components are required to be installed on the user's machine, such as when the test engine 12 is accessed remotely such as via a web browser of the user's machine. Advantageously, the FLEX® applications for each of the components of the applications or methods 14, 20, 26 and 28 may provide a stateful client where changes can occur on the display without requiring to load a new web page. Additionally, it has been determined that such an implementation allows sufficient resolution of geometry and position data to be acquired such that corresponding test results can be analyzed to provide meaningful information about motor, cognitive and cognitive-motor function of the user.

Data is acquired for each test application 26 to 28 as corresponding respective test data 30 to 32, which can be provided to and/or utilized by the analysis engine 16. Thus, by performing a plurality of multi-part tests 26 through 28, each test can provide corresponding test data 30 to 32 that can be analyzed by the analysis engine 16 to provide meaningful information and results based on the test data 30 to 32.

The test data can include an indication of which test of a plurality of different tests is being performed along with an indication of the position of graphical objects (e.g., targets) for the test as well as an indication of the position for a cursor or other pointing device that is utilized for performing the test. For example, the test application 26 to 28 can employ a get_cursor_pos( ) or other Application Programming Interface (API) to monitor and obtain cursor position information that is stored along with temporal information, such as the times corresponding to the obtained cursor positions, as the test data 30 to 32. The sampling of such data may be at a rate of, for example, 30 Hz.

As an example, a test application 26, 28 can display on the display a GUI having one or more targets, each as a graphical object having a shape (e.g., circle, oval, triangle or rectangle) that encompasses or bounds a set of coordinates on the user's display device. A user can position on the display a cursor or other graphical object having its own object position in two-dimensional space (e.g., having X and Y coordinates), for example, using a pointing device, such as a mouse or stylus for touch screen, or without a pointing device, such as via a finger on a touch screen. The test application 26, 28 can provide instructions requesting the user to position the cursor/object or draw lines between two or more particular targets. The movement of the cursor on the screen relative to the known position of each of the targets (corresponding to the test data 30 to 32) can be analyzed by the analysis engine 16.

The analysis engine 16 may include, for example, a motor calculator 34 and/or a cognitive calculator 38. The calculators 34 and/or 38 may be, for example, software modules stored on a computer-readable hardware device, which may be executed to perform various calculations based on the same or different input parameters.

In an example embodiment, the motor calculator 34 is programmed to determine a number of one or more kinematic variables based on the test data 30 to 32. For example, the motor calculator 34 can be programmed to determine a position of the cursor or pointer device, a velocity, an acceleration, a speed and/or a tangential acceleration for each sample of test data acquired during a test interval. For example, the tangential acceleration may be used by the analysis engine 16 as an indication of degree of curvature in user movements.

In an example embodiment, the motor calculator 34 can also determine derivative information of the above-referenced variables, such as corresponding to a measure of how close to the user's line between a pair of targets is fitted to an ideal straight line between the pair of targets. For example, for every data point residing on the ideal straight line between sequential targets, a distance to a corresponding point on the line drawn by the user can be determined. The sum of the determined distances between the respective points can be determined, and divided by the number of points for Which the distances were determined to provide an average associated with the ideal line relative to that drawn by a user. This can be repeated for a line drawn by a user between respective targets to provide an objective indication of the accuracy of lines drawn.

In an example embodiment, the motor calculator 34 may further calculate a means square error by determining an average of the error squared for the difference between the ideal and actual lines. In an example embodiment, the motor calculator 34 may further calculate the root mean squared error or standard deviation of the difference between the ideal and actual lines, for example by calculating the square root of the means square error. Thus, the motor calculator 34 can determine various values representative of the average distance that the user's data points on the user's line deviate from the idea line.

In an example embodiment, average, means square error, root means square error, and/or standard deviation information may be similarly calculated for deviation, over the course of a test, per each recorded position, each separate X position and Y position, and/or on a per line basis, between speed, velocity, acceleration, tangential acceleration, etc., between actual recorded values and ideal values for those parameters.

Other information includes whether the user has drawn crossing lines, as described below with respect to FIGS. 15 and 16.

The above is not intended as an exhaustive list of calculations which the motor calculator 34 may perform, and other example embodiments provide for calculation of additional or alternative variables and parameters based on the acquired test data 30 to 32 that is sampled over time. The results of the calculations determined by the motor calculator 34 can be stored as part of analysis data 36. The analysis data 36 can also include calibration data 24 and patient data 18, which can be utilized to improve the accuracy of the calculations by the motor calculator 34 and the cognitive calculator 38. Alternatively, calibration data may be used, as described above, to alter the administered test, so that results of tests administered at different platforms are comparable, without requiring further consideration of differences between the platforms, e.g., as reflected by the calibration data 24.

In an example embodiment of the present invention, the cognitive calculator 38 is programmed to compute variables or parameters relevant to assessing cognitive function of a patient-user. For example, the cognitive calculator 38 can compute a dwell time based on the acquired test data 30 and 32. A dwell time can correspond to a time period during which a cursor or other graphical object is within a given predefined bounded area, such as can be defined as an X and Y position or range that encompasses a displayed graphical object or target. The computed dwell time may be used to assess a patient's set switching ability, to refocus attention from one task to another, for example, where dwell time reflects a dwell period in a first target (abet initial movement to the first target) before moving to the next target. Dwell time may be an indicator of "cognitive freezing" in neurocognitive or other patient groups. The cognitive calculator 38 can also calculate the reaction time, such as corresponding to a time interval between a presentation of a stimulus and the initiation of movement of a pointing device by a user during a reaction test application 26, 28, which can be further utilized by the cognitive calculator 38 to generate a score of the patient's information processing capacity. In an example embodiment of the present invention, the cognitive calculator 38 may further use data output by the motor calculator 34, e.g., representative of motor function quality, to calculate data representative of cognitive ability.

For example, an initial speed or acceleration when leaving a given target to move to a following target may be used as a cognitive measurement in certain instances. For example, if the initial phase of movement is relatively rapid (with high velocity and acceleration), and the user moves to the correct target, this information may be used to conclude that the user movement was made primarily under predictive or feedforward control (i.e., the user was very sure of where to go). On the other hand, if the speed or acceleration is relatively low or there are multiple starts and stops once the user leaves the target, the information may be used to conclude that the patient is unsure of the target to which to move, indicative of a deficiency in information processing speed, especially where other components of the user movements are relatively normal or can be made relatively quickly. It should be understood and appreciated that certain types of calculations may not apply to different types of tests depending upon the main purpose of the test.

In an example embodiment of the present invention, the analysis engine 16 can output results of calculations to provide corresponding analysis data 36. Thus, the analysis data 36 can include results data based upon the methods and calculations performed by the motor calculator 34 and/or the cognitive calculator 38 based on test data 30 to 32 acquired for each of the respective test applications.

In an example embodiment of the present invention, the analysis engine 16 may include an index calculator 40 that is programmed to compute one or more indices based upon the output results determined by the motor calculator 34 and/or cognitive calculator 38 for a patient. For example, the index calculator 40 can aggregate the analysis data determined for a given set of test data acquired for a given patient to determine an index (or score) having a value indicative of motor function for the given patient based on the aggregate set of test data. Alternatively or additionally, the index calculator 40 can compute an index (or score) having a value indicative of cognitive function for a patient based upon the set of test data. Alternatively or additionally, the index calculator 40 can compute an index (or score) having a value indicative of cognitive-motor function for a patient based upon the set of test data. The index calculator 40 can be normalized according to a known scale or index, such as the UPDRS. Alternatively or additionally, the index calculator 40 can calculate a new scale that provides an indication of motor and/or neurocognitive functions for the patient. The resulting output for the index calculation can be provided and stored as part of the analysis data 36 for subsequent analysis, e.g., by a clinician who may access the stored analysis data 36.

In an example embodiment of the present invention, the system may modify factors used for the index calculation based on the corpus of data for a plurality of patients. For example, if a large number of users who are considered generally healthy perform poorly on a certain test, the test results for that test may be modified by a low weighting factor.

In an example embodiment of the present invention, as a user takes one or more tests, the system may generate analysis data 36 which indicates that the test(s) presented to the user are too difficult or too easy for the user. For example, where calculated scores are extremely low, the scores may indicate that the user is below a certain threshold level of ability, but do not finely indicate the user's level of ability below that certain threshold. Similarly, where calculated scores are extremely high, the scores may indicate that the user's level of ability is above a certain threshold level of ability, but do not finely indicate the user's level of ability above that certain threshold.

Accordingly, in an example embodiment of the present invention, the test engine 12 further includes a module for accessing stored analysis data concerning a current patient and selecting one of the TEST applications 1-N to next output to the user based on past performance indicated by the accessed analysis data. For example, where the test engine 12 determines from the analysis data that the user's performance is below a predetermined threshold, the test engine 12 may select a next test that is ranked as being at a particular low difficulty level. For example, difficulty may be ranked according to target accuracy (i.e., the size of the displayed targets (e.g., relative to calibrated screen size)) and/or distance between the displayed targets (e.g., relative to calibrated screen size). For example, a test having targets at a first distance from each other and of a first size may be ranked as easier than another test of the same type having targets that are at a second distance from each other, longer than the first distance, and/or that are of a second size, smaller than the first size. In an example embodiment, the change in test difficulty may be implemented by re-administering the same type of test as a previously administered test, with changes to the target accuracy and distances and thus chances in the difficulty level of the re-administered test.

In an alternative example embodiment, the change in test difficulty may be implemented by selecting a different type of test, which test type is ranked at a different difficulty level than that of a previously administered test.

In an example embodiment of the present invention, during administration of a test, the analysis engine 16 may produce part of the analysis data 36 associated with the test, even before completion of the test. During the test, the test engine 12 may access the partial analysis data 36 produced for the test prior to its completion, and may modify the current test during its administration based on the partial analysis data 36. For example, during the administration of the test, the test engine 12 may enlarge previously displayed targets of the test and/or shorten the distance between the previously displayed targets. Alternatively or additionally, where the test dynamically displays targets during its administration, the test engine 12 may display new targets that are larger than those previously displayed, or at distances that are shorter than the distances between pairs of previously displayed targets.

Figure 2:
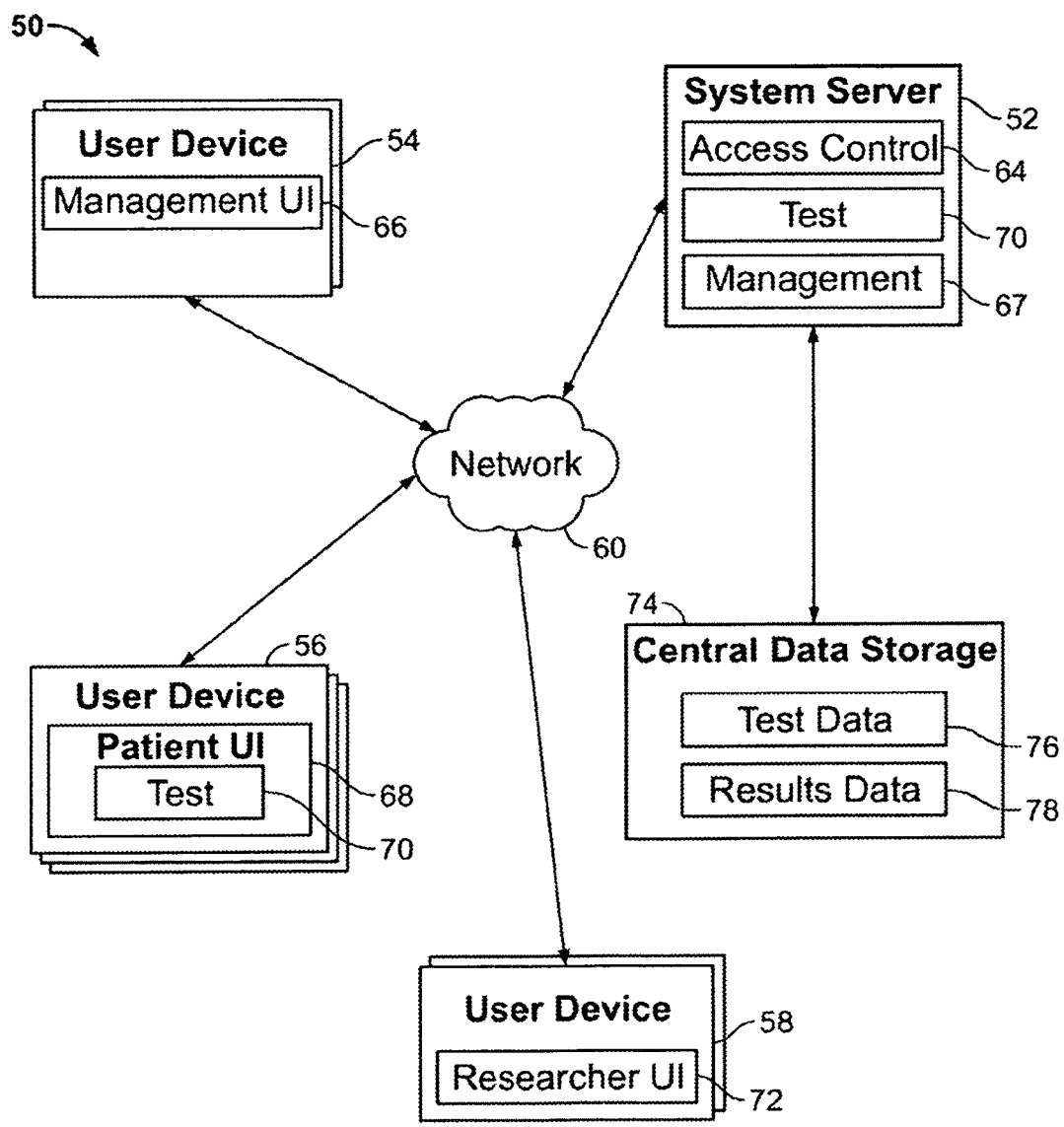
FIG. 2 depicts a system architecture that can be implemented for testing and analysis of motor and cognitive functions, according to an example embodiment of the present invention.

FIG. 2 depicts an example of a network system 50, including an example architecture for performing testing, analysis and/or evaluation. In the example of FIG. 2, the system 50 includes a system server 52 that is programmed to provide methods and functions for use to implement various methods remotely at user devices indicated at 54, 56 and 58. Each of the user devices 54, 56 and 58 is connected to or can communicate with the system server 52 via a network 60. The network 60 may include a local area network (LAN), wide area network (WAN) (e.g., the Internet) or a combination of networks, including private and public domains, as is known in the art.

In an example embodiment, the system server 52 may include a web server having a plurality of different functions and methods, each of which can be accessed via a corresponding resource locator, such as a uniform resource location (URL). In an example, the system server 52 includes an access control function 64 that provides a level of security such that only authorized users can access various other functions and methods of the system. The access control function 64 can provide a log-in user interface screen to each of the user devices 54, 56 and 58, which can require a user ID and password for each user for authentication. Each user ID and password can be associated with a corresponding level of authorization to selectively provide access to one or more of the other functions and methods to be provided by the server system 52. While FIG. 2 illustrates devices 54, 56, and 58 as separate devices, the operations of each may be performed on a single device, but may be logically separated according to the log-in information. In an example embodiment, a single set of log-in information may provide authorization for access to operations of more than one of the shown devices 54, 56, and 58.

Figure 26:
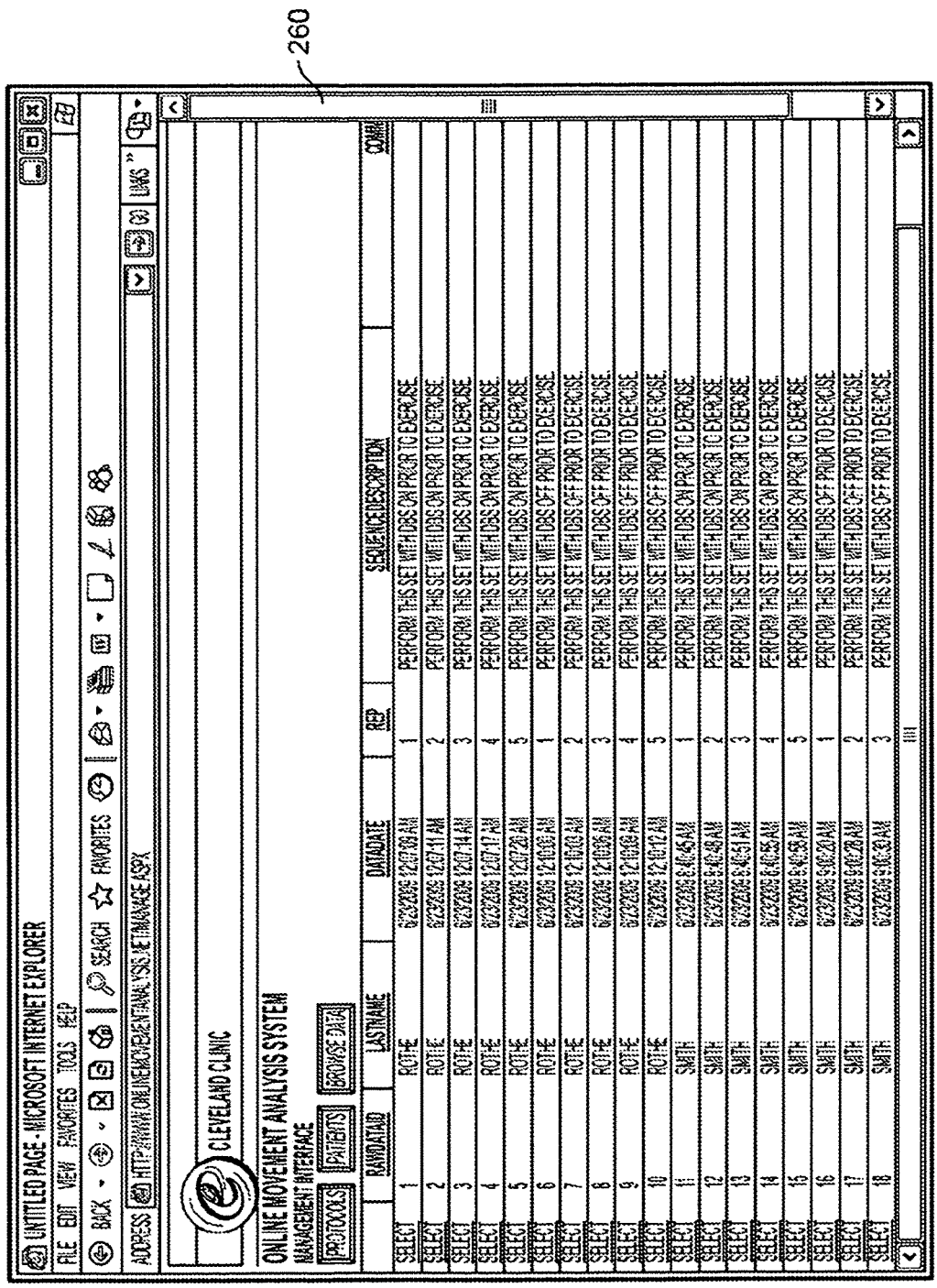
FIG. 26 depicts a screen shot for another management user interface that can be utilized for browsing and selecting patient test data, according to an example embodiment of the present invention.
Figure 27:
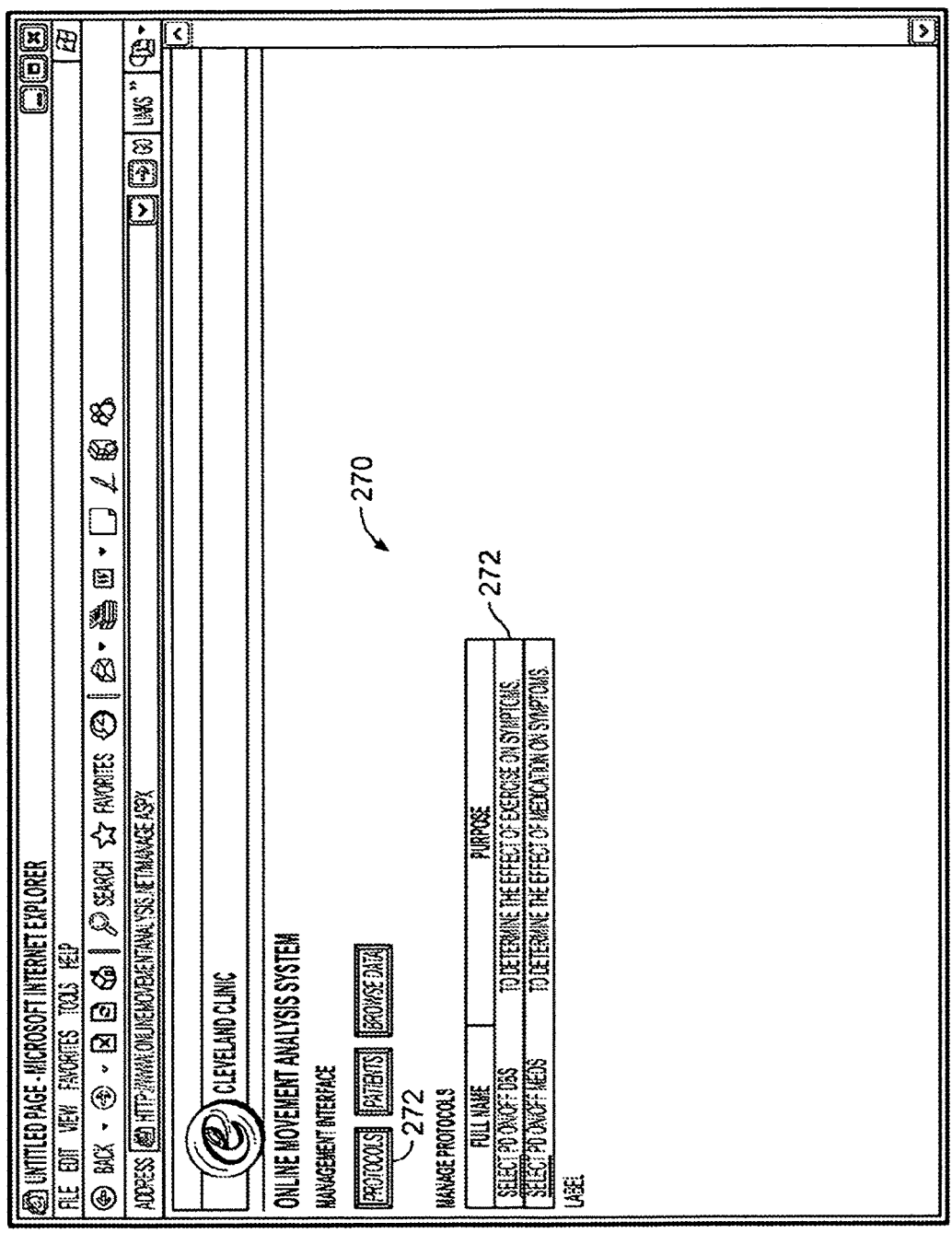
FIG. 27 depicts another management user interface that can be utilized for managing patient protocols employed during testing, according to an example embodiment of the present invention.

For example, the user device 54 can be assigned a high or unlimited authorization level and utilized to provide one or more management user interfaces 66, for accessing each of the functions and methods provided by the server system 52, including accessing corresponding management functions and methods indicated schematically at 67. Thus, the authorized user of the management user interface 66 can access various management functions 67 for the patient information, browsing test data and the like. For example, the user interface 66 may be a clinician interface via which a clinician may access test results for tests taken by the clinician's patients or other related information. Examples of selected management user interface screens are shown in FIGS. 26 and 27.

The user device 56 can include a patient user interface 68 that can provide a limited amount of access such as to the testing functions and methods 70. For example, after logging in via the access control function 64, a patient user interface 68 can be used to access the test applications 70, which can be graphically displayed in the patient GUI. The test applications can be provided as interactive web pages programmed with functions and methods for performing various tests and obtaining patient-controlled movement information from the patient-user.

The test methods 70 that are provided to the patient user device 56 via the patient user interface can be implemented using ADOBE® FLEX® or another similar software or platform having a high market penetration. By having a sufficiently high market penetration, substantially no software needs to be installed or loaded onto an individual user's device. In response to interaction with the tests provided via the test methods 70, test data 30 to 32 may be obtained by the system server 52 for storage in a central data storage 74 (described in further detail below). Methods of the analysis engine 16 may be performed locally at the patient user device 56 or remotely at the system server 52.

Examples of associated graphical user interfaces associated with the testing functions and methods that can be presented to the user are shown and described herein with respect to FIGS. 4-20.

Another user device 58 can include a research user interface 72 that provides access to relevant data (e.g., excluding patient identifying information) such as to facilitate research and analysis of the test data. For example, a researcher or other authorized user can access a set of test data for a plurality of patients and, in turn, perform statistical methods or other mathematical operations on the set of data to ascertain relevant information, such as correlations or likelihoods. A researcher might also utilize the analysis data to draw correlations between other information entered by the user (e.g., patient data, including an identification of medications, dosage and the like) relative to test results for each of a plurality of users. Such analysis can provide information that can be stored in the central data storage 74 for subsequent usage and review by other authorized users. For example, correlations can be drawn between medication and test results and changes in test results over time, which correlations can be presented to a physician or other authorized user via the management user interface 66.

Alternatively or additionally, certain patient devices can be preconfigured having a preset authorization status, such that authorization would not be required. Such devices known to the system server 52 can access the system server 52 through the network 60 or through a secure local area network or other suitable connection. For instance, such preconfigured terminals can reside at doctors' offices, hospitals or other institutions.

In an example embodiment, regardless of the configuration and distribution of patient user devices 56, the test data is consolidated into a database or other central data storage 74 that is associated with the central system server 52.

The central data storage 74 can include raw test data 76 and results data 78. While central storage 74 is shown as a single storage device and/or logical storage location, in an example embodiment, the raw test data 76 may be stored separate from the results data 78, e.g., for quicker response time to results data queries.

The raw test data 76 and results data 78 can be indexed by patient and by individual test as well as include patient specific information (in an example embodiment, excluding patient identifying information other than perhaps a patient unique identify number) for purposes of separating the patient data from one patient from that of another patient. As described herein, the test methods 70 and the system server 52 can be programmed to perform calculations on the raw test data acquired from a patient user interface via the testing application being implemented thereon.

Similarities between patients residing in a given, cluster (i.e., patients who share certain characteristics) can be utilized to facilitate treatment and diagnosis of other patient's having similar conditions. For example, a clinician may enter information (e.g., patient information with respect to medication (type and/or dosage), stimulation parameters (e.g., of a DBS therapy), symptoms, conditions, and/or diagnoses) via the management user interface 66, which can be tagged (or programmatically linked) to the test data and results data of the patient, such as to augment or provide metadata that can be further evaluated or considered to facilitate clustering of patients and understanding the respective conditions. In this way, the test data for a more statistically significant population can be maintained for performing statistical analysis of test data, which can be mined or otherwise evaluated statistically or otherwise, e.g., via the researcher user interface, to understand the correlations of symptoms and conditions. For example, the system of the present invention may be queryable for test result data by symptom(s) and/or diagnosis, in response to which the system may return results data 78 concerning those patients matching the symptom(s) and/or diagnosis, and/or averages and/or other aggregate data of the results data 78.

In an example embodiment, the system and method of the present invention may provide for a clinician, using the user device 54, to input a proposed change, e.g., with respect to medication (type and/or dosage) and/or stimulation parameters (e.g., of a DBS therapy), for a particular patient for whom patient information and test results have been obtained. In response to a query triggered via user-selection of a command at the user device 54, the system server 52 may search the central data storage 74 for patients associated with patient data and test data similar (by a predetermined degree) to those of the particular patient. The server may further search for those of the patients who have been subjected to a change similar to that proposed for the particular patient and for whom subsequent test results data have been obtained. The server may output for display at the user device 54 an average of such subsequent test results, thereby indicating to the clinician an expected change in the particular patient's condition with the proposed change, measured in terms of expected change in test results.

Alternatively or additionally, the system may output a medical condition category corresponding to the average of such subsequent test results. For example, different intervals of test scores may be associated in memory with different categories of cognitive and/or motor skills. The category under which the average of the subsequent test results falls may be output. Alternatively or additionally, the expected direction of change to the medical condition classification may be output, e.g., whether the cognitive and/or motor skills are expected to improve or decline.

FIGS. 3 through 27 show example screen shots or other graphics for presentation in a user interface, to provide a general understanding of the algorithms and functionality that can be implemented by the systems 10 and 50 shown and described with respect to FIGS. 1 and 2.

Figure 3:
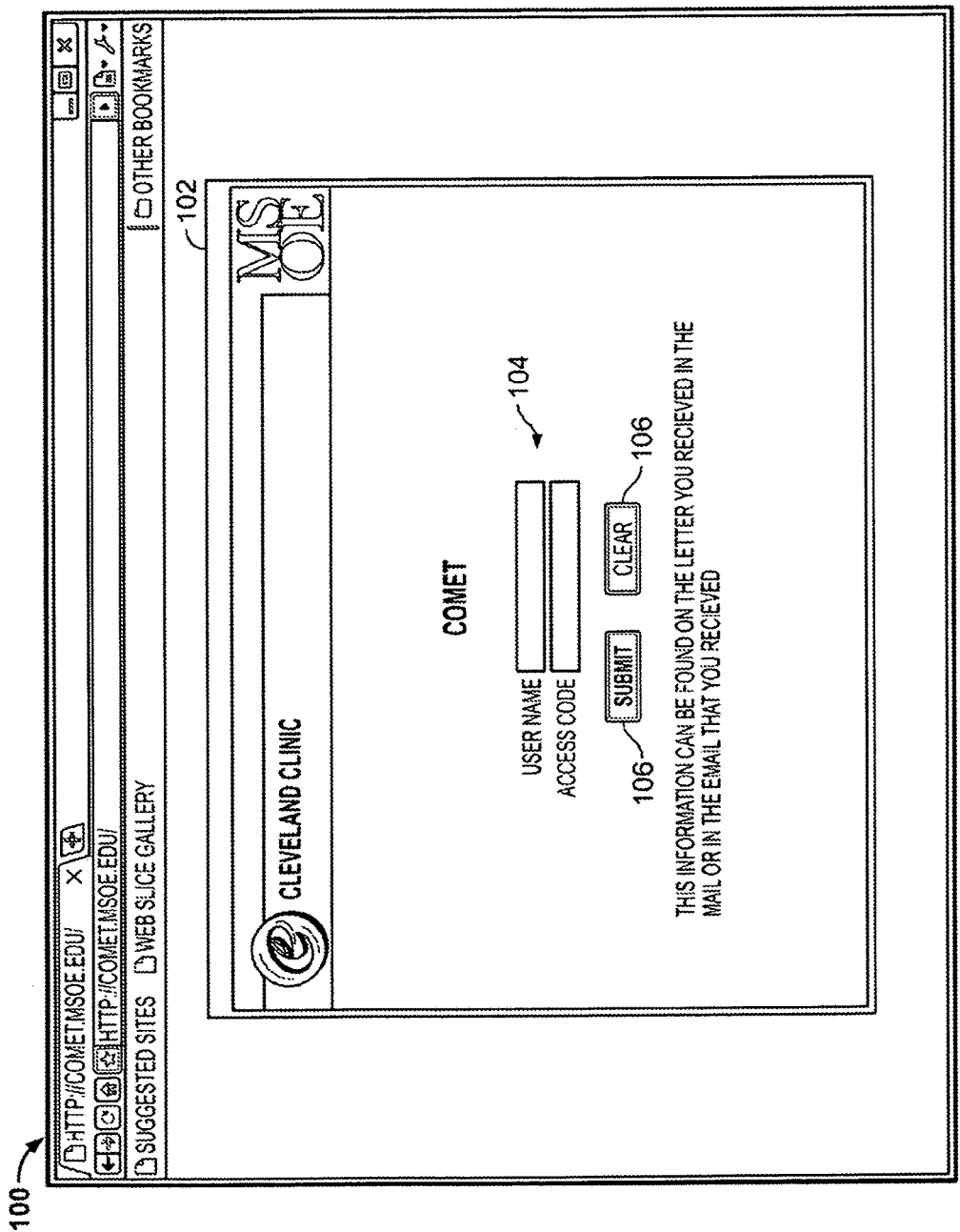
FIG. 3 is a screen shot for a log-in screen, according to an example embodiment of the present invention.

FIG. 3 depicts an example of a screen shot 100 including a GUI element 102 that can be utilized for access control into the system, as described in detail above. The GUI element 102 includes user entry fields 104 that can be utilized for obtaining a user name and access code for authorized use of the system. Graphical buttons or others graphical interface elements 106 can be provided for submitting or clearing information with respect to the user entry fields 104.

Figure 4:
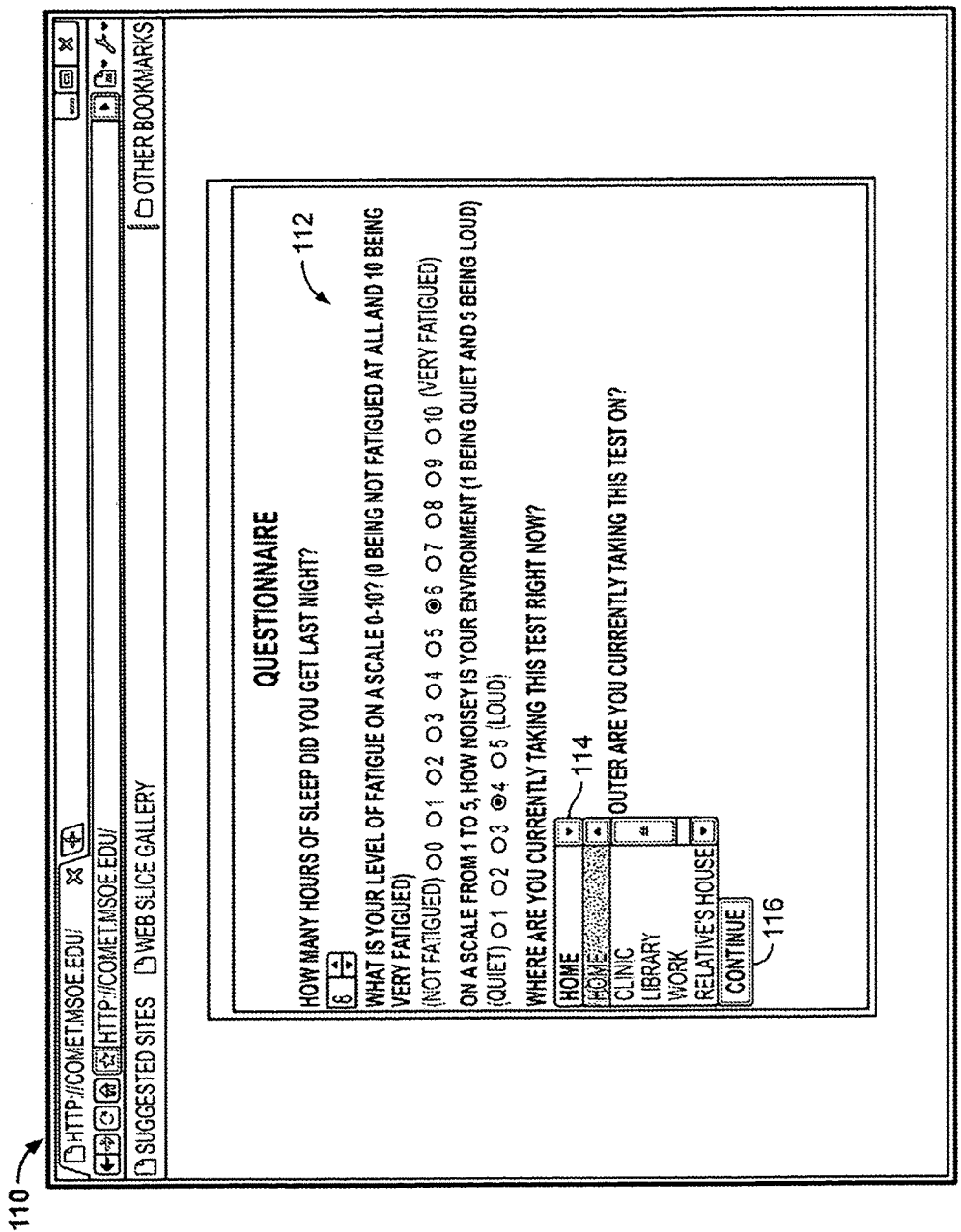
FIG. 4 depicts a patient's questionnaire that can be presented to a patient or clinician user, according to an example embodiment of the present invention.

FIG. 4 depicts an example of a screen shot 110 including an example of a GUI element 112 for obtaining information pertaining to a user's general health condition, state of mind and environment in which the test is being taken. For example, the questions may include: "How many hours of sleep did you get last night?"; "What is your level of fatigue on a scale of 0-10?"; "On a scale from 1 to 5 how noisy is your environment?"; "Where are you currently taking the test right now?" Associated with this or other questions can be a drop down context menu 114 that can be utilized by the user to identify and select one of a predetermined number of responses. After answers to the question(s) have been entered, a user can hit a continue user interface element (a graphical button) 116 to continue.

Figure 5:
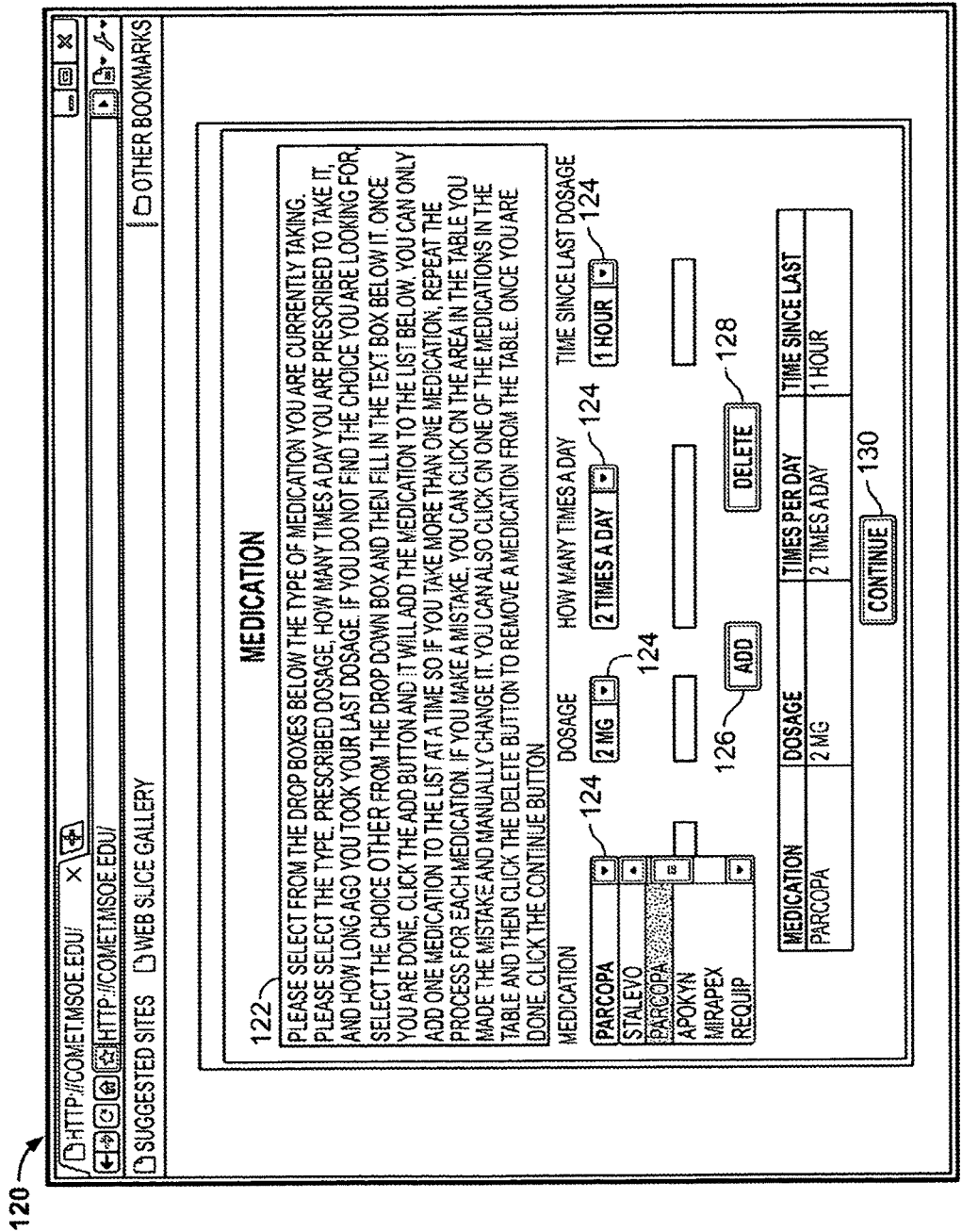
FIG. 5 depicts a screen shot for another part of a questionnaire that can be presented to a patient or clinician user, according to an example embodiment of the present invention.

FIG. 5 depicts another screen shot example 120 that can be utilized to obtain information about medication that a given patient may be taking. The screen shot 120 includes a GUI element 122 having a variety of drop down context menus that can be utilized to identify medication(s), dosage, number of times per day the medication(s) is taken, and time(s) since last dosage of the medication(s). After the particulars associated with a given medication have been entered via the drop down context menus 124, a user may enter them into the system via an add user interface element 126. Similarly, an entry can be deleted or removed by selecting it with a cursor or other user interface element and in turn hitting a delete user interface element 128. After all medications have been appropriately entered into the medication form GUI element 122, a user can continue to the next phase of the testing process by hitting a user interface element or button 130. The medication information can be programmatically associated with test data to allow correlations to be determined, such as described herein. In an example embodiment, a clinician may enter some or all of the medication and/or other therapy inhumation into the system.

Figure 6:
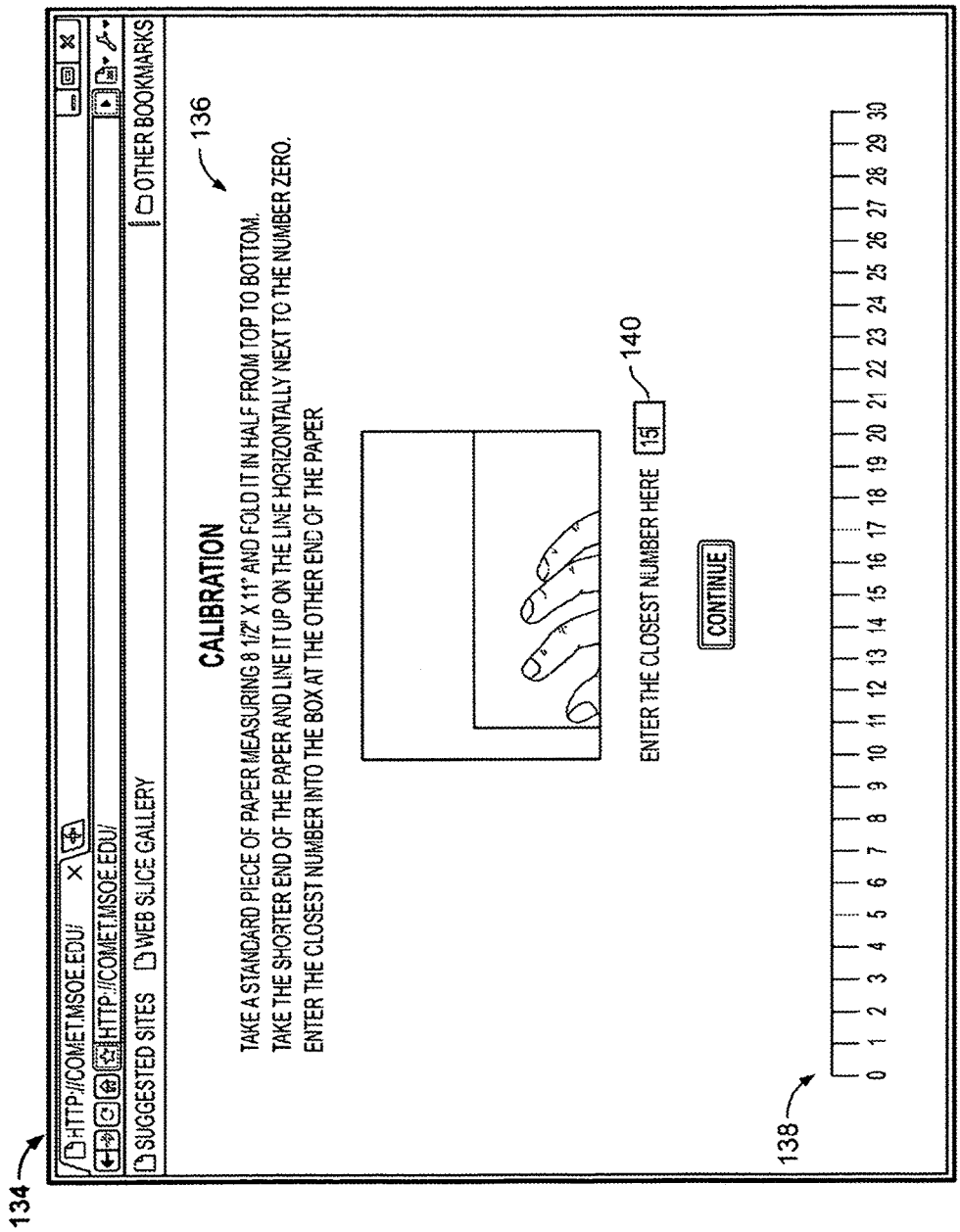
FIG. 6 depicts a graphical user interface (GUI) that can be utilized for calibration of a remote test device, according to an example embodiment of the present invention.

FIG. 6 depicts an example of a screen shot 134 demonstrating a calibration GUI 136 that can be implemented for calibrating a remote user's computing device in a horizontal direction, according to an example embodiment of the present invention. The calibration GUI 136 presents the user a scale 138 having a plurality of spaced apart markings or indicia, which are numbered consecutively in the example of FIG. 6 from zero to thirty. The calibration GUI 136 presents instructions to the user to fold a 8.5"×11" sheet of paper in half and place the shorter end of the folded sheet of paper adjacent the scale 138 with the one of the longer sides against the zero, and to enter the number closest to the other of the longer sides in a user entry dialogue box 140. The number entered into the dialogue box 140 relative to the actual size of the paper can be utilized to determine a size or dimensions of the display area presented on a user screen during the testing process. A similar calibration can be utilized in a vertical direction on a user screen such that both the horizontal and vertical dimensions can be known such that the results from the testing can be scaled appropriately.

Figure 7:
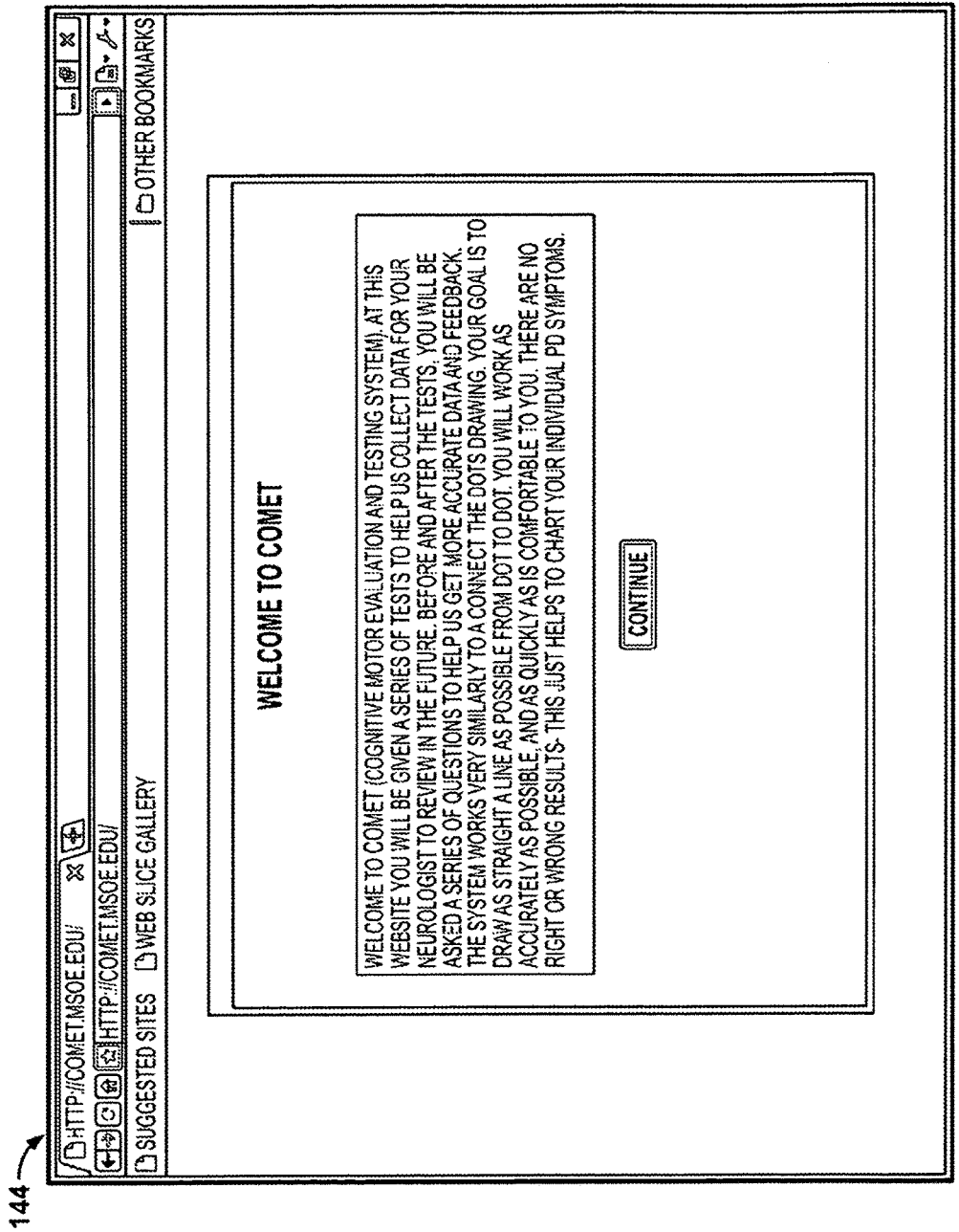
FIG. 7 depicts a screen shot GUI for an introductory screen that can be utilized for initiating a test, according to an example embodiment of the present invention.

FIG. 7 depicts an example of a "welcome" screen shot that can be presented to the user to inform the individual that a test is about to begin and identify some additional information about the types of the test and how they will proceed. It should be understood that a few practice screens and tests can be implemented before beginning an actual test to familiarize a user with the testing process.

Figure 9:
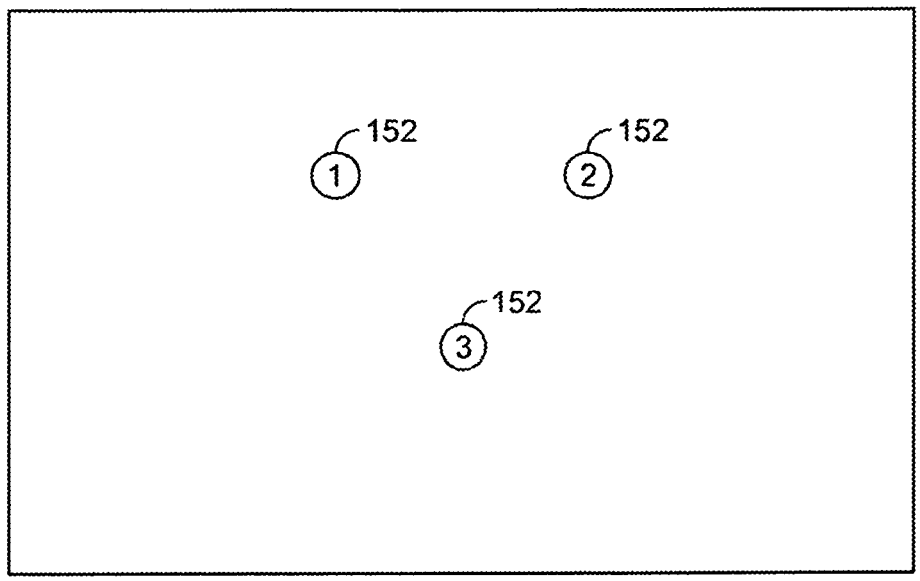
FIG. 9 depicts a "seven's test" GUI that can be implemented on a computer, according to an example embodiment of the present invention.
Figure 10:
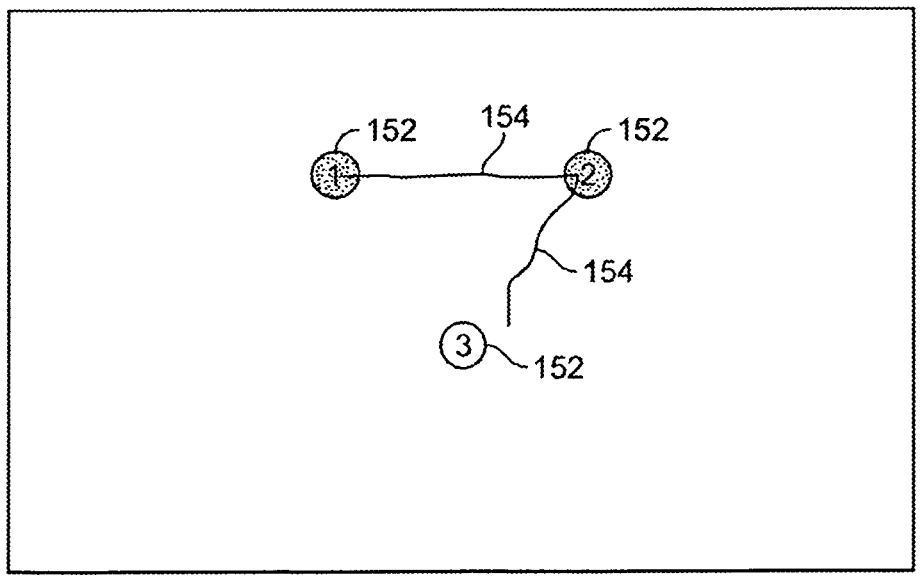
FIG. 10 depicts the "seven's test" GUI of FIG. 9 illustrating the test completed by a user, according to an example embodiment dale present invention.

FIG. 8 depicts an example of an instruction GUI 146 that can be provided before performing a first test. FIGS. 9 and 10 depict an example of GUI 150 that includes a plurality of targets 152 for use in performing a "seven's test", for which a user is instructed to draw between targets a path having a shape similar to the number "7", for testing cognitive and/or motor skill. Each of the targets can be graphically constructed, as a graphical object that encompasses a region in the X/Y coordinates of a patient's graphical interface, such as in a screen. The GUI 150 corresponds to an example of a traditional "seven's test" in which a user is instructed to connect the dots using a pointing device such as a mouse, stylus, touch screen or the like. In the example of FIG. 9 three targets numbered numerically 1, 2, 3 are presented on the screen. A user is instructed to connect the targets 1 to 2 to 3 to draw a shape similar to the number "7". The system may record test data in association with performance of the test. The test data may include, for example, the position and temporal information of the path taken for connecting the targets. FIG. 10 shows an example of an outcome of a patient having connected target positions 1 and 2 but not target positions 2 and 3. To indicate the successful connection of target positions 1 and 2, the system has highlighted targets 1 and 2, in contrast target 3 which is not highlighted. Referring back to FIG. 1, the test data acquired from FIG. 9 can include an identification of the position of each of the targets, a path taken by the patient for connecting or attempting to connect the targets, and/or temporal information associated with the path.

Thus, the information obtained with respect to the test outcome shown in FIG. 10 may include the coordinates of each of the targets 152 as well as the coordinates (or position) of the cursor or other pointing element during the test as the cursor or other pointing element moves between the respective targets and forms a corresponding line or path 154.

FIG. 11 depicts an example of an instruction GUI 158 that can be provided before performance of a second test.

Figure 12:
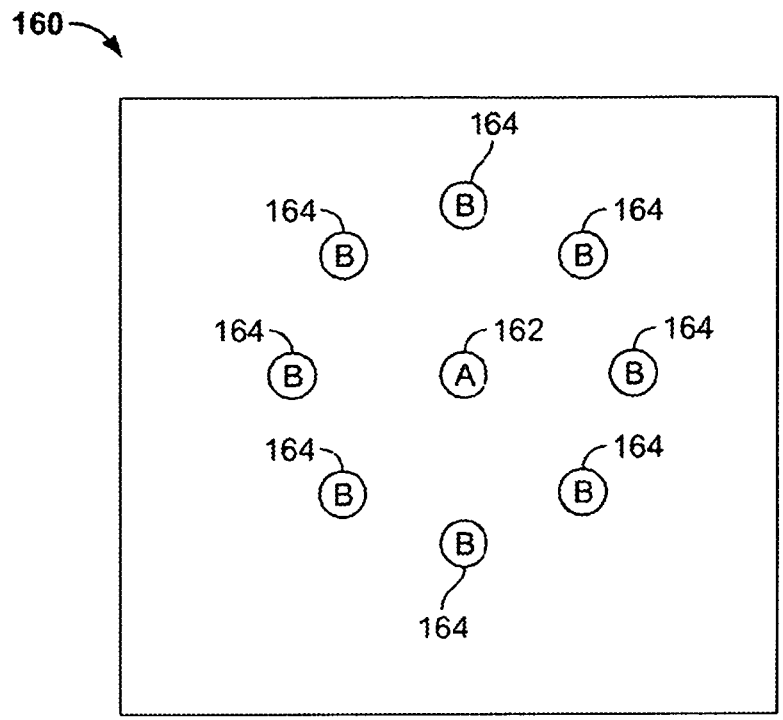
FIG. 12 depicts a reaction test GUI that can be implemented on a computer, according to an example embodiment of the present invention.
Figure 13:
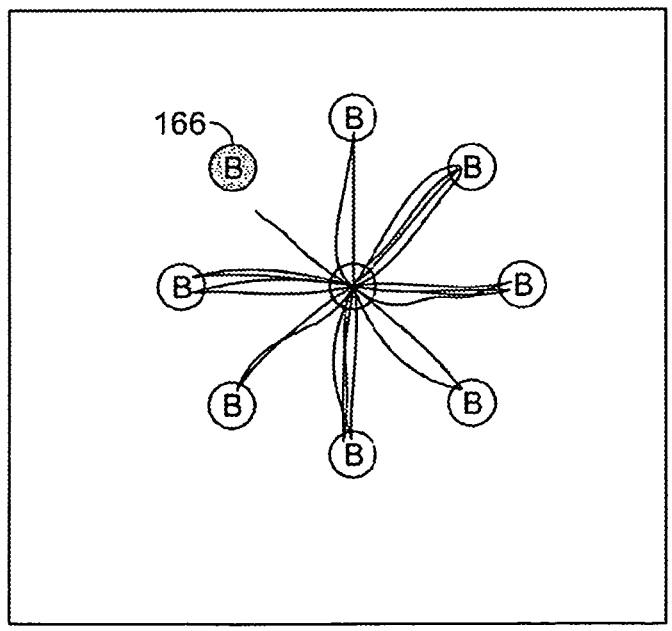
FIG. 13 depicts the reaction test GUI of FIG. 12 at least partially completed by a patient user, according to an example embodiment of the present invention.

FIGS. 12 and 13 depict an example of a GUI 160 that can be provided in connection with performing a reaction time test with subsequent movement, such as a center-out test, for testing, e.g., cognitive ability. Thus, the GUI 160 includes a plurality of targets, including the center target 162 and a plurality of outer targets 164 in circumscribing relation relative to the center target. The center-out test can be performed to test reaction time of the user by displaying one of the outer targets 164 in a contrast color relative to the other targets 162 and 164 and in turn storing the time interval from displaying the contrasted target on the GUI 160 to the time the user begins to move a pointing device for connecting the central target 162 to the contrasted outer target 164. Additional information can be obtained during the process, including the position over time of the cursor relative to each of the respective graphical renderings of the targets, e.g., representing a path taken by the user between the center target 162 and the outer targets 164, and/or the corresponding times.

In FIG. 13, a partially completed center-out test is depicted showing one of the targets 166 having a contrast color relative to the other targets thereby designating the intended target for connection between the center target 162 and the contrast target 166. The center-out test can be performed such that different ones of the outer targets are selected in a predictable or random order one or more times.

Figure 15:
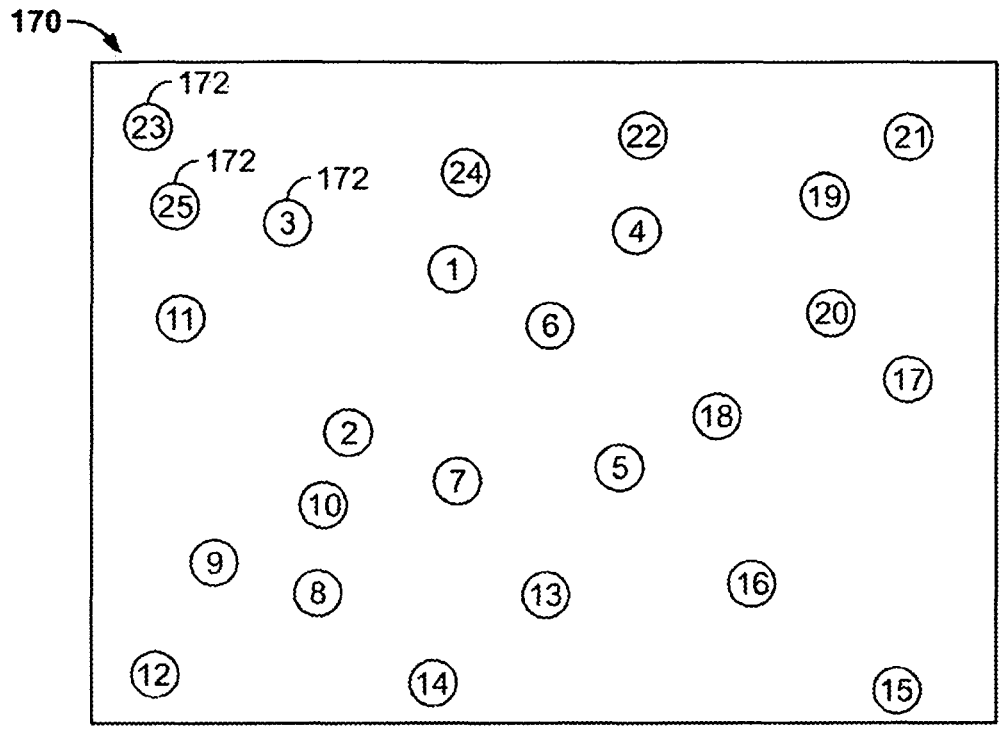
FIG. 15 depicts a trail making test (Part A) GUI that can be implemented on a computer, according to an example embodiment of the present invention.
Figure 16:
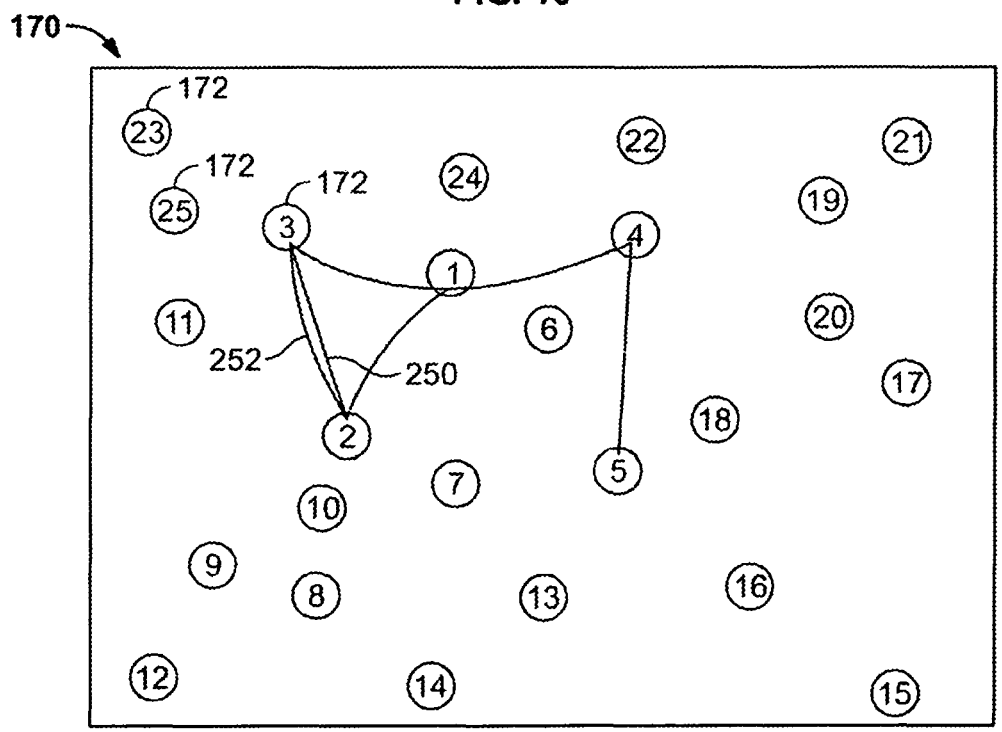
FIG. 16 depicts the trail making test (Part A) GUI of FIG. 15 partially completed by a patient user, according to an example embodiment of the present invention.

FIG. 14 depicts an example of another instruction GUI 168 that can be presented to a user fen providing instructions for performing a third test, including such as shown and described with respect to FIGS. 15 and 16.

FIGS. 15 and 16 depict an example of a test GUI 170 that can be utilized for performing a trail making test (Part A), for testing cognitive and/or motor skill. The trail making test (Part A) implemented via the GUI 170 may be used to assess both motor and cognitive information concurrently. For instance, a plurality of targets 172 are distributed across the display area provided by the GUI 170. In the example of FIGS. 15 and 16, the targets are numbered from 1 to 24 and the user (as instructed by the instruction GUI 168 of FIG. 14) is to connect the targets in a sequential order. The test engine can populate the display area for the GUI 170 in a pseudo random fashion such that each of the sequential targets can be interconnected by an ideal straight line without crossing a line interconnecting any other sequential targets. Thus, in addition to obtaining the position, velocity, speed and/or acceleration information, crossing lines can also be identified to provide a further indication of a patient's motor and cognitive function.

FIG. 16 depicts an example in which a patient has connected the first five targets with lines going from target 1 to target 2 to target 3 to target 4 and to target 5. Thus, from the example tests of FIGS. 15 and 16 information corresponding to the position of the cursor that is utilized to draw each line connected between sequentially numbered targets can be recorded and stored as test data in memory (e.g., local or associated with a server). In addition to the position data, temporal data can be obtained with each sample as well. Thus, the position and time data can then be provided as test data to the analysis system for evaluation, such as she and described in further detail below.

Also depicted in FIG. 16 is a diagrammatic view of a line used in an analysis that can be performed to characterize a degree of error, e.g., by calculating an average error, a mean square error, or a root mean square error, for each of a plurality of respective lines interconnecting sequential targets 172 in the GUI 170. For example, referring to targets 2 and 3, this can be performed, for example, by comparing the relative positions of points along an ideal straight line 250 connected between targets 2 and 3 relative to a line segment 252 drawn by patient (e.g., responsive to user-controlled movement with a pointing device) between the same respective targets. For instance, the same number of equally spaced sample points can be populated along the length of each line segment 250 and 252 and a corresponding means square error can be computed for differences between the sets of sample points. For example, the error values recorded for the sample points can be squared, then summed together, and then divided by the number of sample point pairs to provide the mean square error of the patient's line 252 relative to the ideal line segment 250. Those skilled in the art will understand and appreciate various types of estimators that can be utilized to compute a measure of how close the user's line 252 is to the fitted ideal (straight) line 250 between targets, such as including the sample mean, sample variance, analysis of variance, root mean square error, standard deviation as well as linear regression techniques.

For example, the resulting mean square error can further be utilized to compute a root means square error by taking the square-root of the mean square error for each of the line segments between targets. The root means square error thus can provide essentially an average measure of distance of the user's data points on the line 252 from corresponding points on the ideal line 250.

Figure 18:
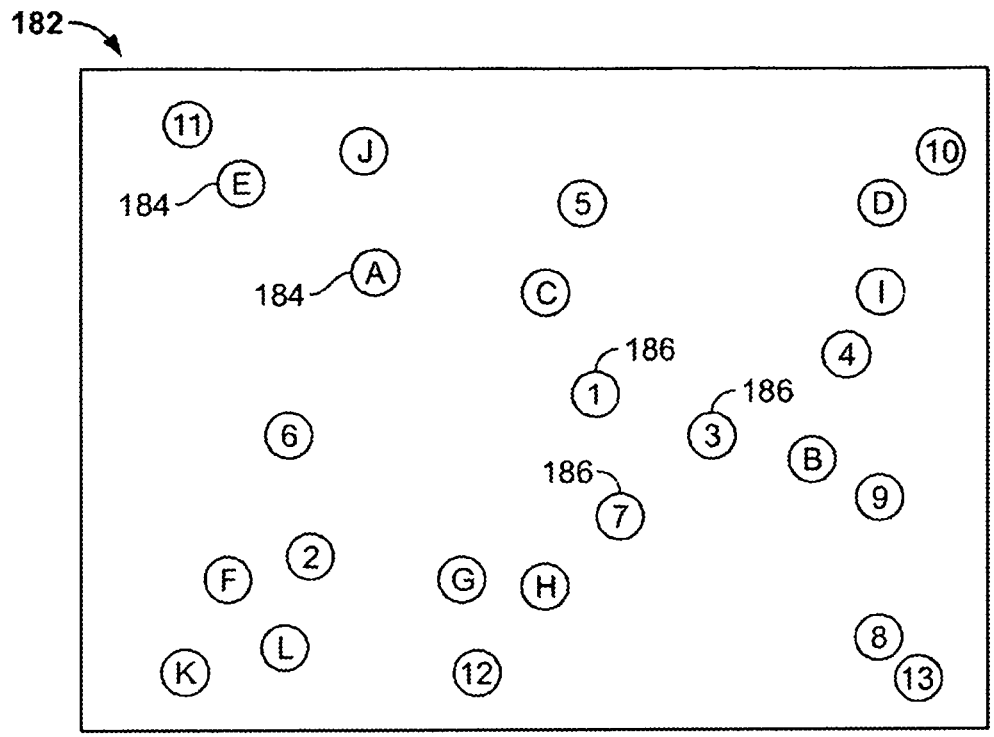
FIG. 18 depicts a trail making test (Part B) GUI that can be implemented on a computer, according to an example embodiment of the present invention.
Figure 19:
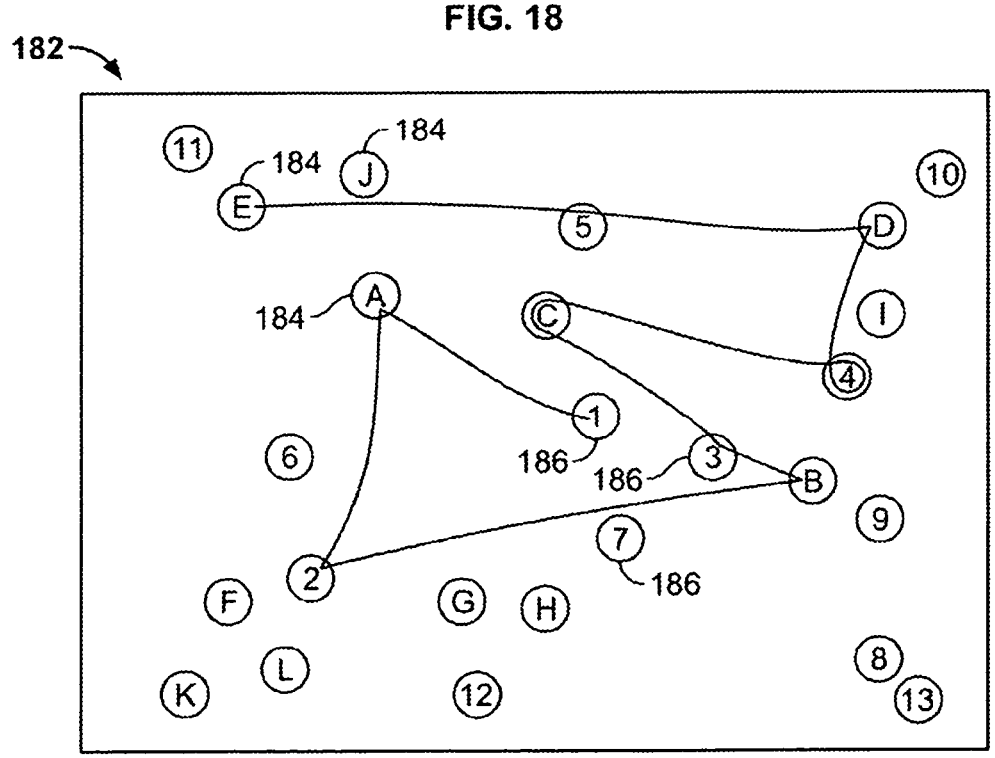
FIG. 19 depicts the trail making test (Part B) GUI front FIG. 18 partially completed by a patient user, according to an example embodiment of the present invention.

FIG. 17 depicts an example of an instruction GUI 180 that can be provided for instructing a user for a trail making test (Part B) test such as shown in FIGS. 18 and 19, for testing cognitive and/or motor skill.

FIGS. 18 and 19 depict an example of a GUI 182 that can be presented to a user in connection with performing and recording information associated with a trail making test (Part B). The GUI 182 presents a plurality of targets positioned in a display area according to application data determined by a corresponding test application. In the examples of FIGS. 18 and 19, the targets are circles, each of which defines a bounded region having a corresponding set of coordinates. In the display GUI 182, a portion of the targets, indicated at 184, have letters ranging consecutively from A through H and another corresponding portion of the targets, indicated at 186, have numbers ranging consecutively from 1 through 13. Those skilled in the art will understand that the test engine can be programmed to automatically generate any arrangement of targets consistent with the format of the trail making test (Part B), which arrangement may be part of the test data provided to the analysis engine 16.

The trail making test (Part B) implemented by GUI 182 may be used to assess both motor and cognitive information concurrently. For instance, the instructions (e.g., via the instruction GUI 180 of FIG. 17) specify that a user-patient is to alternate between consecutive sequential letters and numbers by connecting respective targets with straight lines, similar to what is shown in FIG. 19 up to letter E, beginning with the lowest number to the lowest letter, to the second lowest number, to the second highest letter, etc. Thus, FIG. 19 shows an example outcome of a test in which a user has used a cursor having a position that can be tracked via the corresponding API. The system is configured to dynamically render a graphical depiction of a line onto the display GUI 182 in response to movements of the cursor, for example, via a corresponding pointing element, such as a mouse, stylus or touch screen. Information associated with the position and times associated with the positions, representing times for each of the movements, can be recorded for subsequent analysis and evaluation as described herein.

Figure 20:
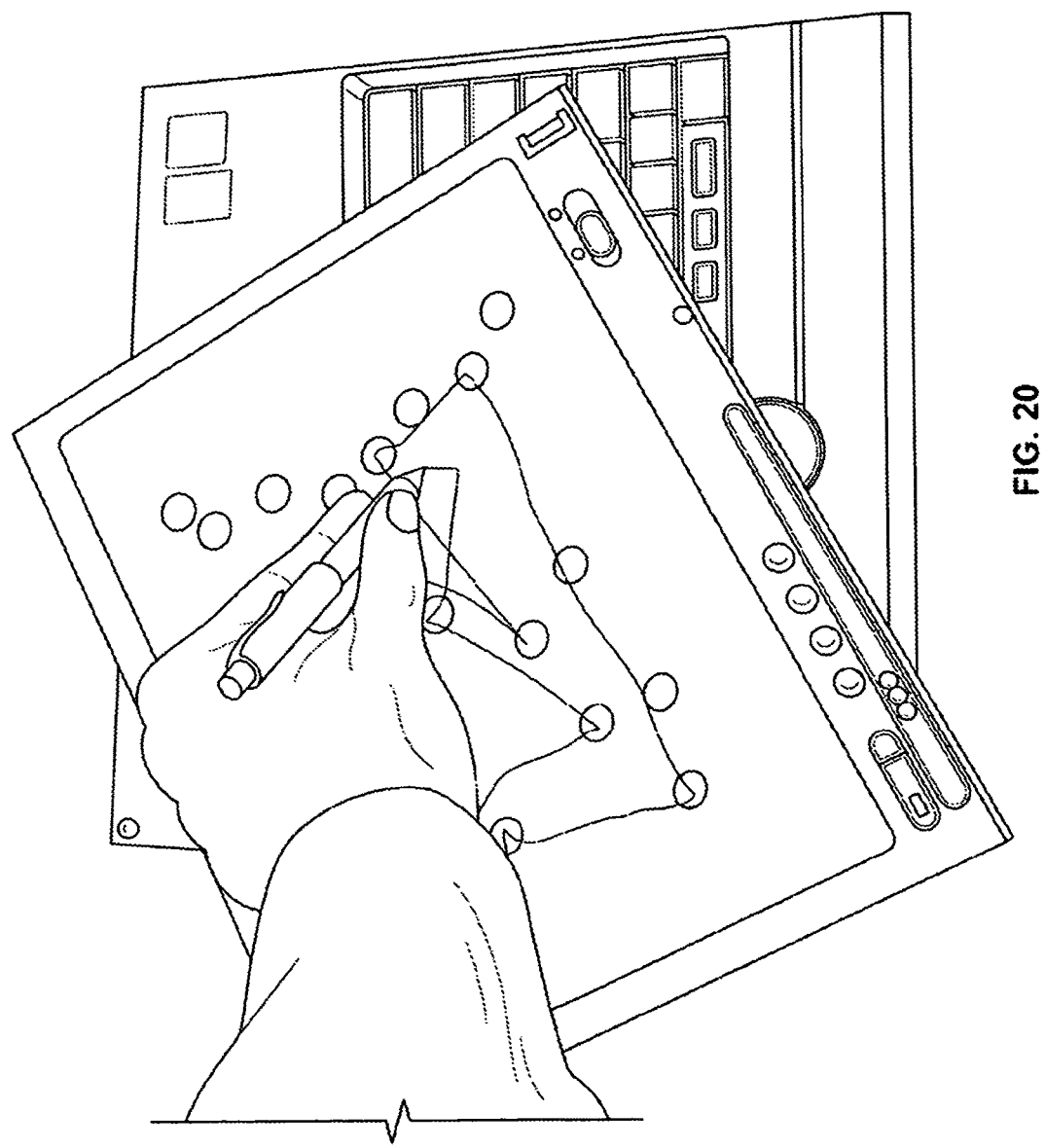
FIG. 20 depicts a trail making test being performed on a surface of a tablet personal computer (PC) by a patient user, according to an example embodiment of the present invention.

FIG. 20 depicts an example embodiment in which the user computing device for performing a test is implemented as a tablet personal computer (PC). Thus, in this example a user holds a stylus (similar to a pen) on a corresponding touch screen for drawing interconnecting lines between targets, such as is shown in FIG. 18. It is understood that a user could use the user's fingers to draw the interconnecting lines.

Figure 21:
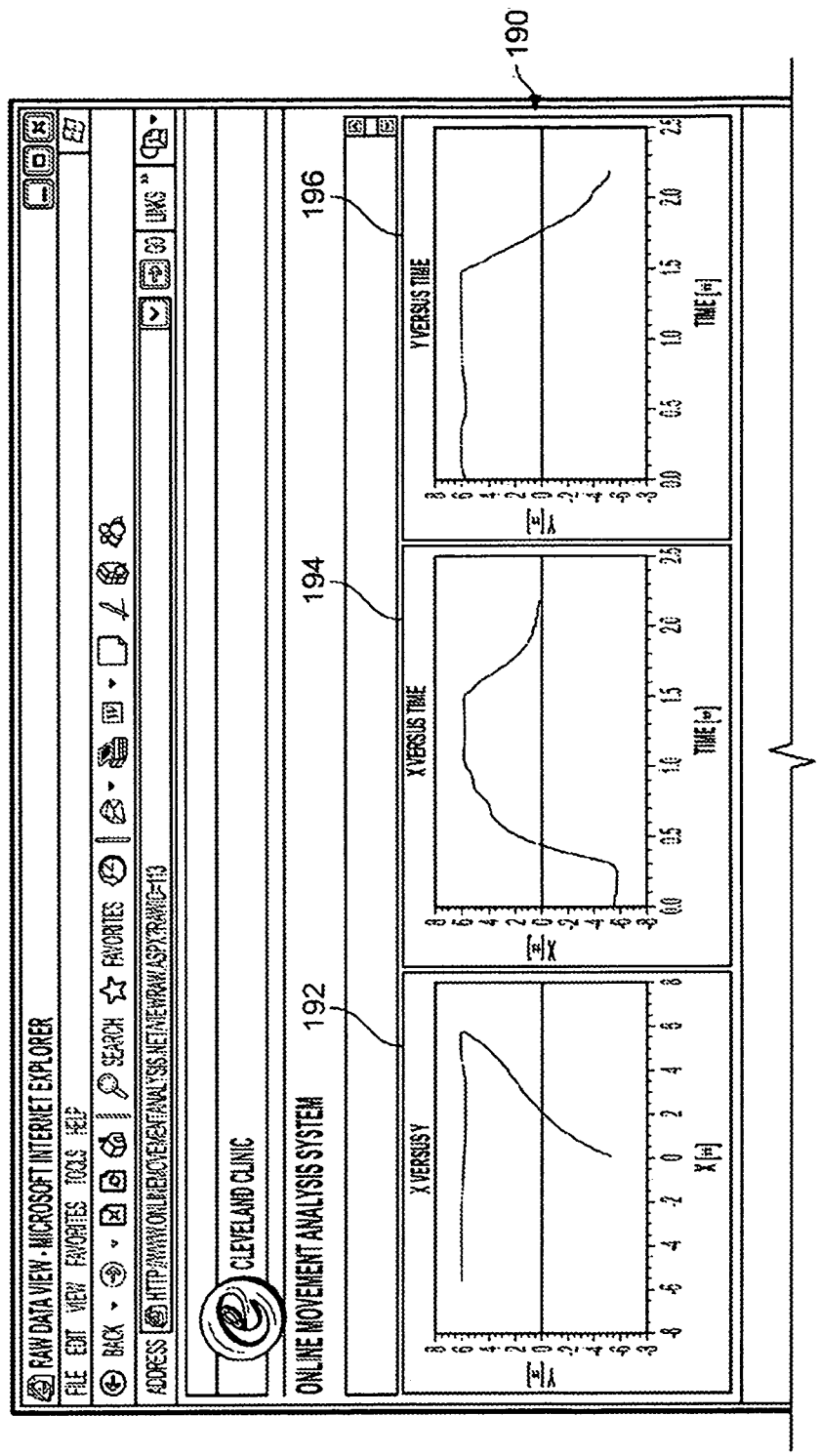
FIG. 21 depicts test results that can be displayed to a user via a management user interface, according to an example embodiment of the present invention.
Figure 21:
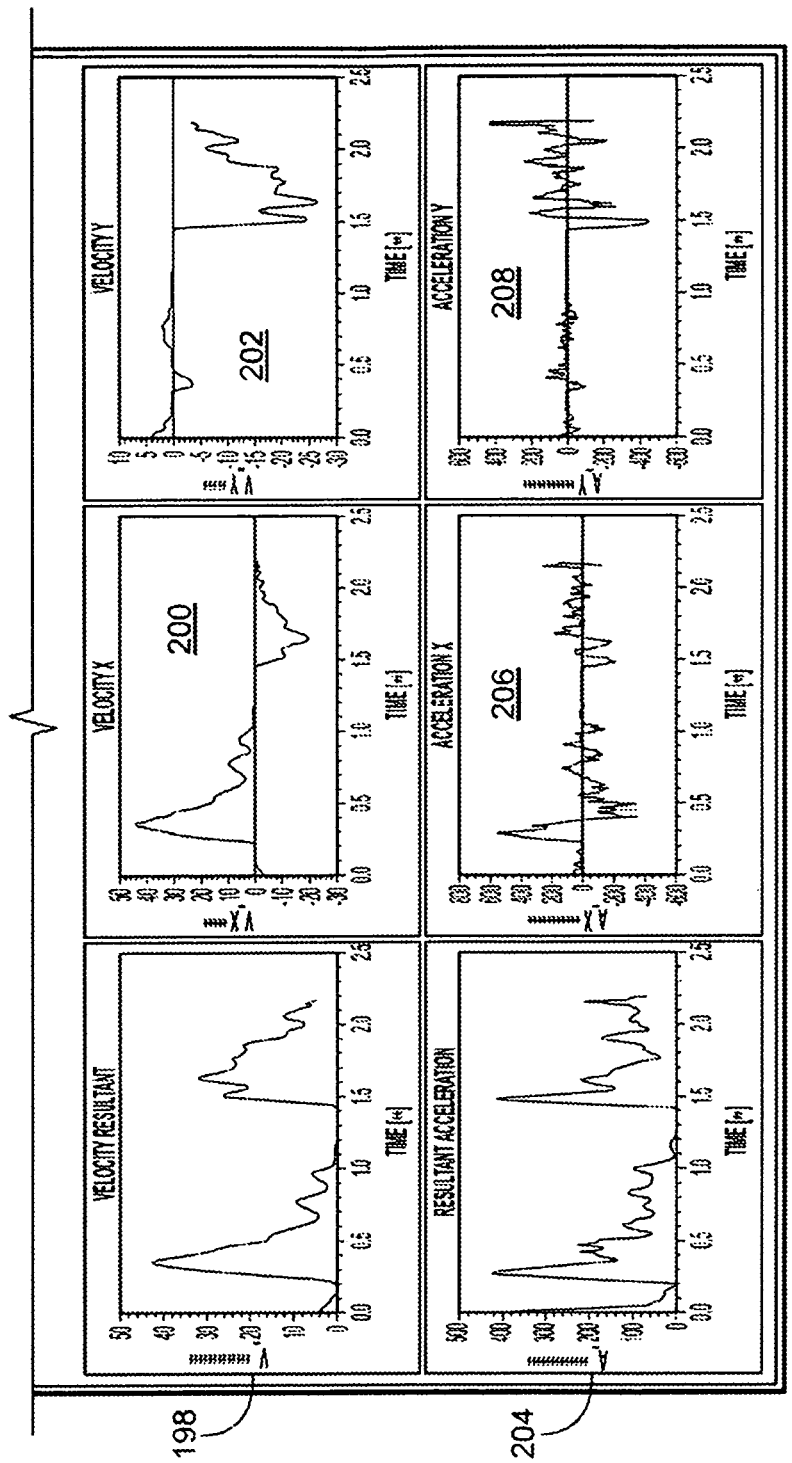

FIG. 21 depicts an example of analysis data that can be generated and displayed in a GUI 190 as a function of test data acquired from a respective test. The resulting analysis data can be presented in a variety of formats, which may be selected by a user. In the GUI 190, a plurality of different plots are shown for depicting different information that can be computed based upon the acquired position and respective time data for a given test. Each of the plots in the top row indicates position information, the middle row of plots indicates velocity information and the bottom row indicates acceleration information for a given test. The position data can be correlated into corresponding velocity and acceleration information by analysis of change over time of the X and Y coordinates of the cursor obtained from the samples recorded during a test. In the example of FIG. 21, the GUI depicts analysis data for a "seven's test" such as shown and described with respect to FIGS. 9 and 10, The GUI 190 can be presented via a management user interface 66 or researcher user interface 72 for analysis and evaluation by an authorized user.

By way of example, the plot 192 depicts X position versus Y position, thereby showing the graphical object as a pair of interconnected line segments in a relative coordinate system based upon user input with a corresponding pointing device, representing the path the user took between the targets of the "seven's test." A representative plot 194 shows the X data of plot 192 plotted as a function of time, and plot 196 shows the Y data of plot 192 plotted as a function of time.

A plot 198 depicts the velocity information corresponding to the changes in the X, Y positions plotted in plot 192 over the time period in which the changes occurred, i.e., during the test. Plot 200 depicts velocity in the X direction with respect to time such as by taking the change between plotted positional points in plot 194 over the plotted time in which such change occurred. Similarly, plot 202 depicts velocity of the Y direction with respect to Time such as by taking the change between plotted positional points in plot 196 over the plotted time in which such change occurred.

Figure 23:
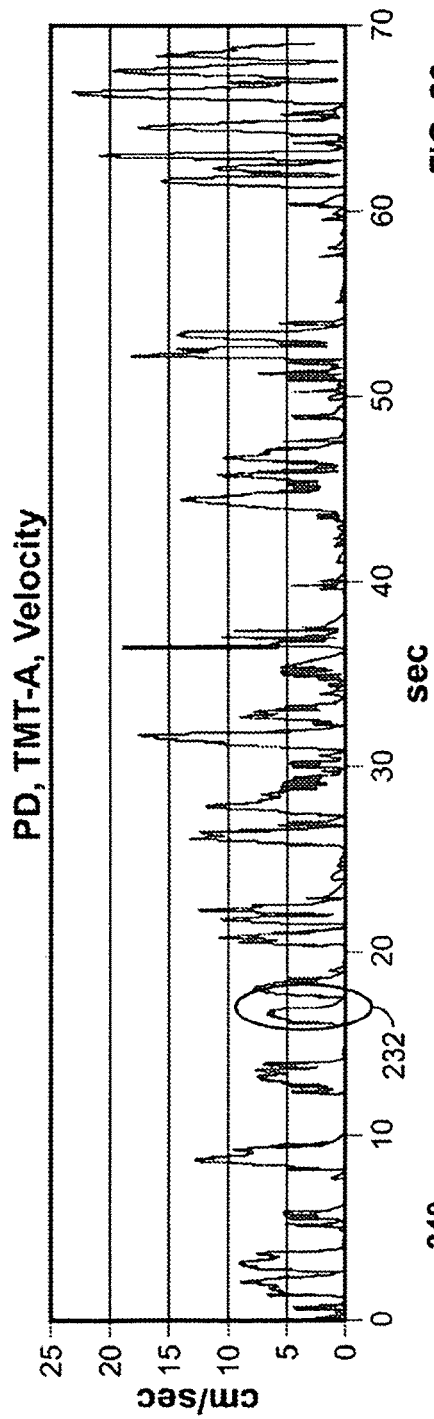
FIG. 23 depicts velocity data that can be computed for a trail making test (Part A) according to an example embodiment of the present invention.
Figure 24:
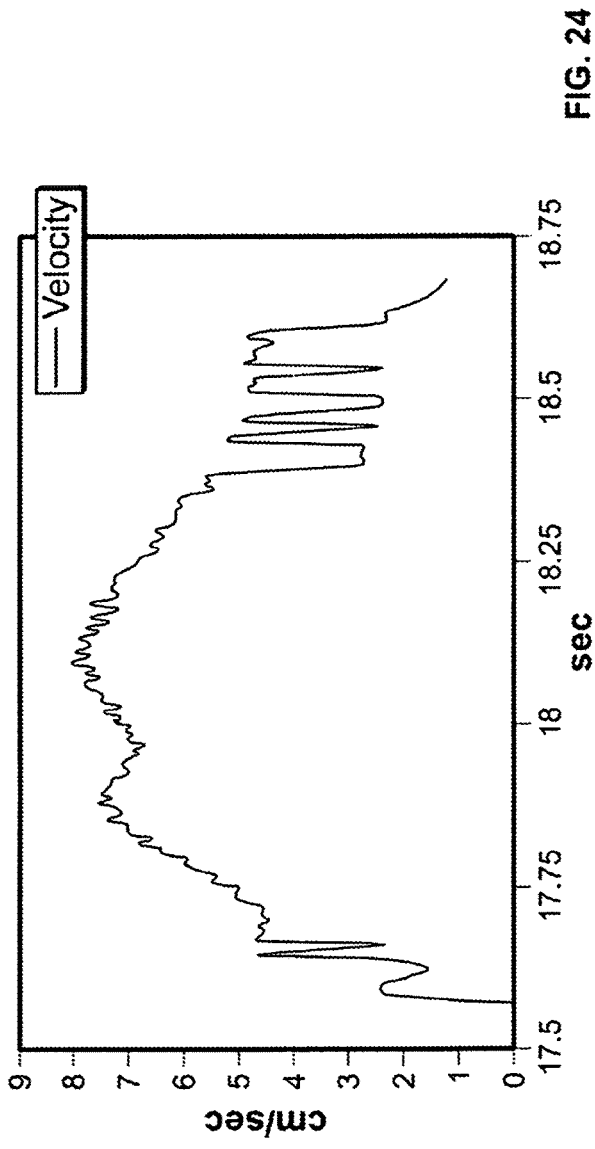
FIG. 24 depicts an enlarged view of a portion of the test from FIG. 23 that can be generated based upon data acquired from a patient user, according to an example embodiment of the present invention.

Similarly, FIG. 23 depicts a plot 230 of velocity as a function of time (cm/sec) that can be obtained from data acquired from a trail making test (Part A) implemented according to an aspect of the invention. An enlarged view of a portion 232 of the waveform formed by the plot 230 is depicted in FIG. 24 at 240.

Referring again to FIG. 21, another set of plots 204, 206 and 208 depict the acceleration for each of the respective curves. For instance, the plot 204 displays a plot of acceleration versus time, such as by taking the change in velocity values of plot 198 over the corresponding time period in which such change occurred. The plot 206 corresponds to the acceleration in the X direction versus time such as by taking the change in velocity values of plot 200 over the corresponding time period in which such change occurred. Similarly, the plot 208 displays a plot of acceleration in the Y direction versus time, such as by taking the change in velocity values of plot 202 over the corresponding time period in which such change occurred.

The separate data concerning the movement in the X and Y directions, respectively, e.g., one or more of plots 194, 196, 200, 202, 206, and 208, may be used, for example, to characterize skill with respect to different directions.

As noted above, the index calculator 40 may calculate a score characterizing a test taker's performance on one or more administered tests. In an example embodiment of the present invention, the analysis engine 16 may compare an overall curve shape of one or more of the types of graphs shown in FIG. 21, e.g., which plot velocity and/or acceleration, to stored graph shapes. For example, the shape of a plotted velocity or acceleration may be compared to a stored smooth bell-shaped curve, which may be considered to represent ideal motion by a healthy person when raking a test. The analysis engine 16 may score the graphs of the test taker's motion, such that the closer the shapes of the graphs to the stored graph shapes, the higher the score. Similarly, the analysis engine 16 may determine the extent (with respect to number and/or degree) to which the graph(s) include spikes, where such spikes may be used as indications of low quality movement including significant and/or many corrective and/or tremor-like motions.

The graph shape score(s) may be used, for example, by the index calculator 40, to calculate the index, which may be stored and output, for example, via the management user interface 66. It is noted that the index may be based on a number of factors. In an example embodiment, different factors, e.g., including the graph shape score, may be multiplied by respective weighting values, for example, depending on ranked significance with respect to the overall index.

Figure 22:
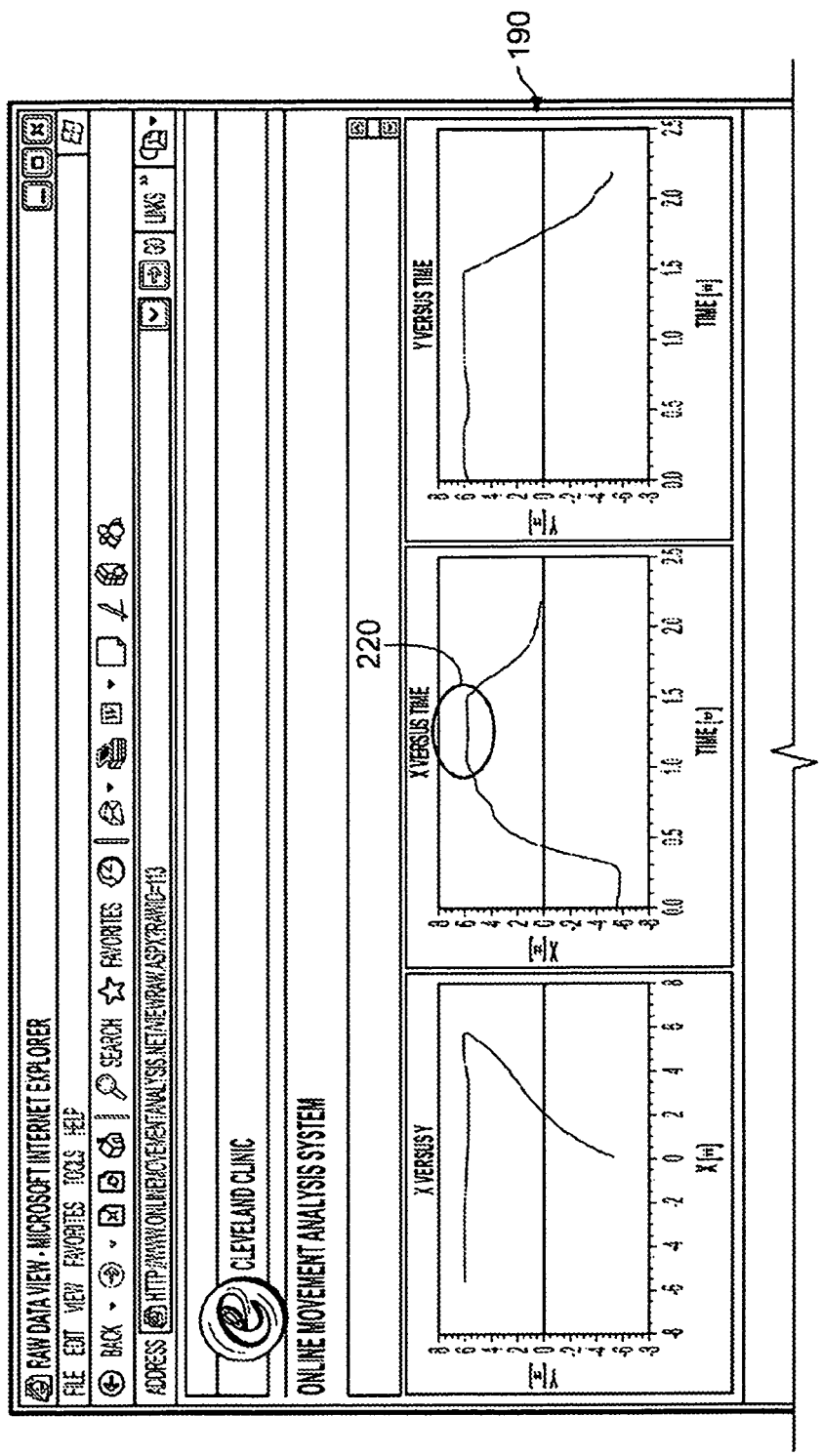
FIG. 22 depicts the management user interface of FIG. 21 demonstrating an example of where data can be obtained for use in assessing neurocognitive functions of a patient user, according to an example embodiment of the present invention.
Figure 22:
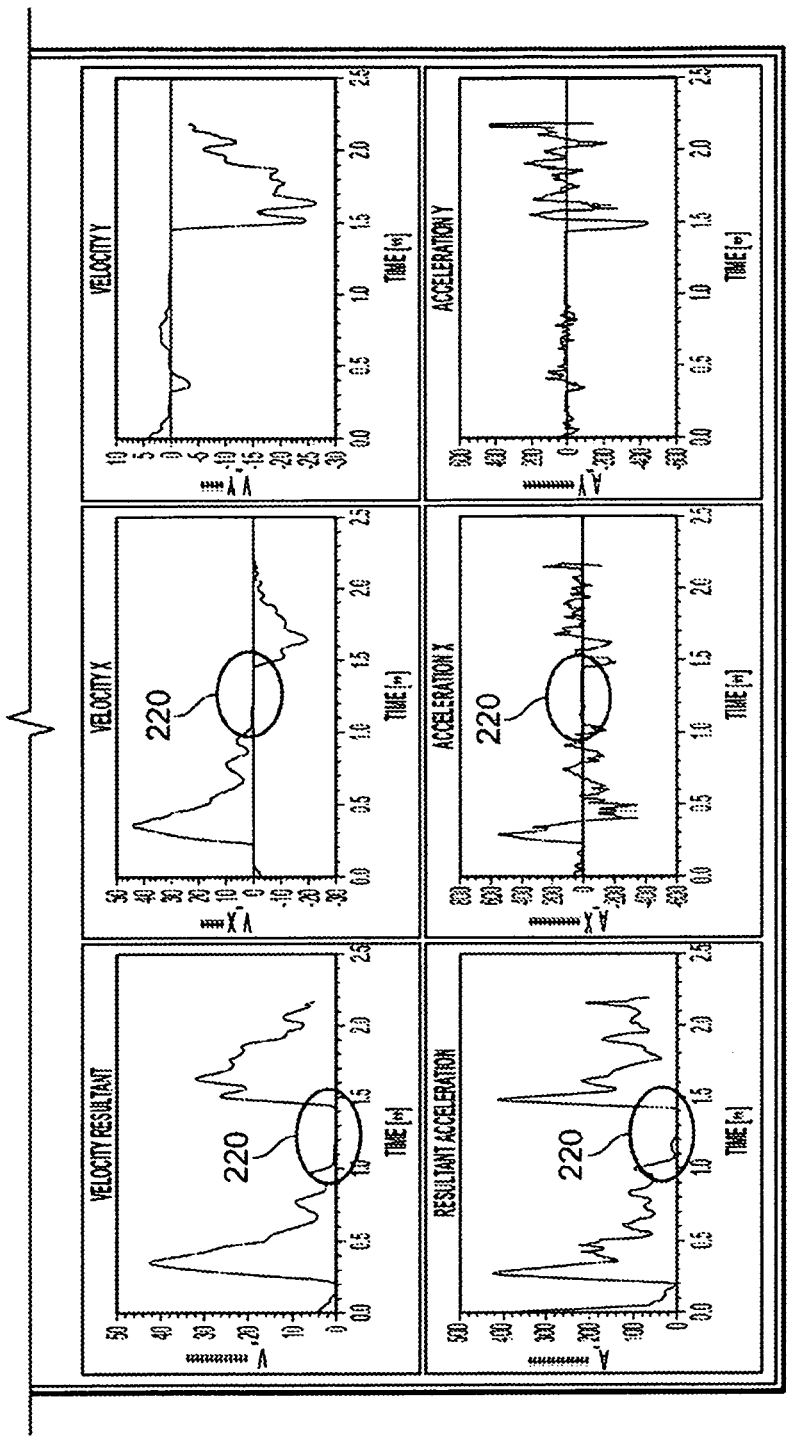

By way of further example, FIG. 22 is a reproduction of the GUI 190 shown in FIG. 21 in which selected portions of position and kinematic data have been identified by circles 220 corresponding to relevant data that can be utilized by the cognitive calculator 38 for computing dwell time. For example, dwell time can correspond to an amount of time that a cursor or other user-controlled graphical interface element resides within a bounded region, such as a defined border of a target. Such bounded regions can be identified in the testing data according to position data (e.g., X and Y coordinates) for each of the targets populating a test GUI. The identified regions for which dwell time is calculated can be identified by identifying the X and Y positions corresponding to each time during which no change occurs in the X and Y position or a period in which there is no velocity (e.g., from plot 198).

Figure 25:
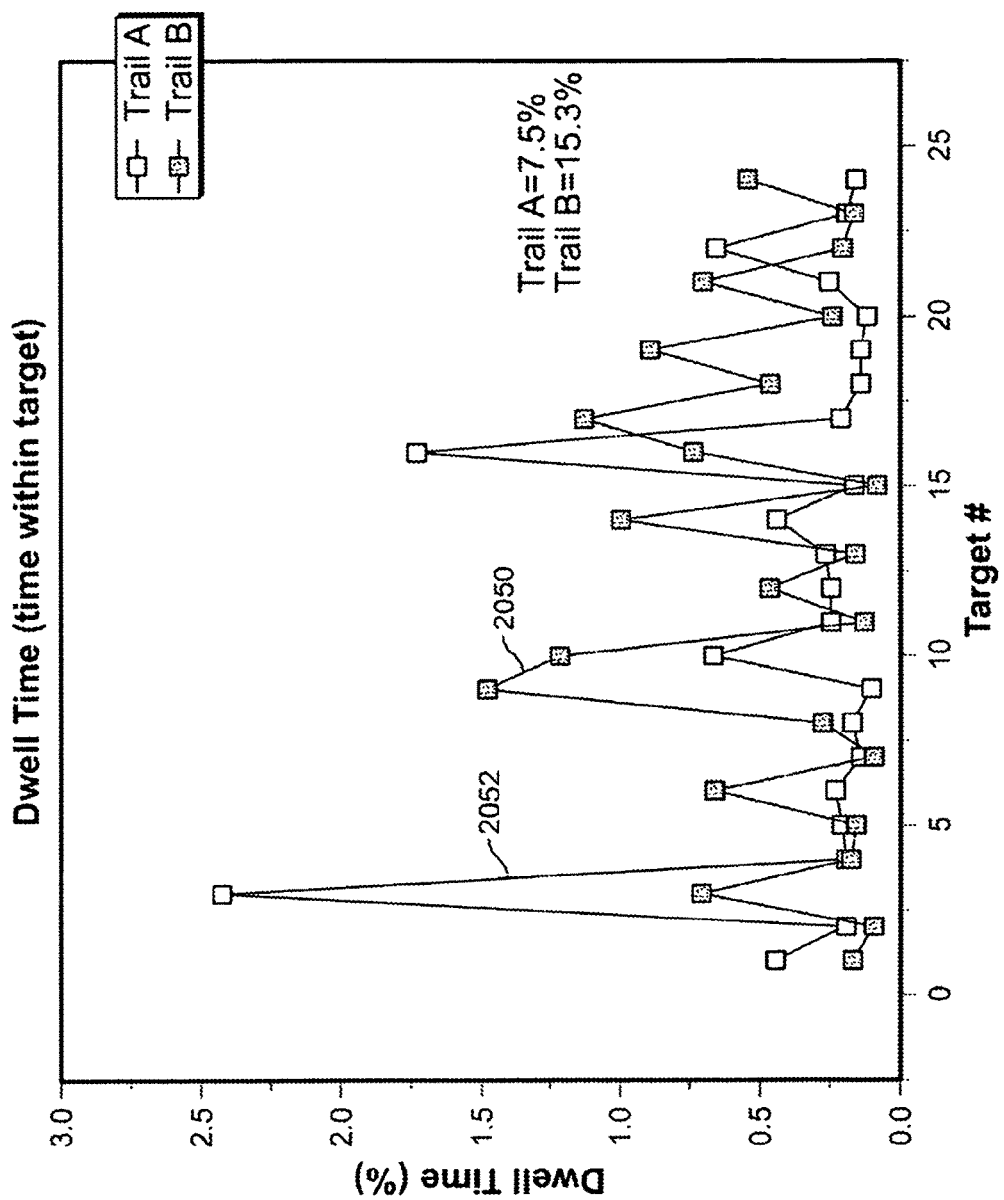
FIG. 25 depicts dwell time data computed for a plurality of targets for a trailing making test (Part A) and a trail making test (Part B) test, according to an example embodiment of the present invention.

FIG. 25 depicts example plots 2050 and 2052 of dwell time that can be computed for a trail making test (Part A) and a trail making test (Part B), respectively. The abscissa corresponds to target number displayed in the trail making tests, and the ordinate corresponds to the percentage of the overall time of the duration of the administered tests in which the cursor dwelled in the corresponding target. As described above, the dwell time corresponds to a time during which a cursor/pointing object is within a given pre-defined X-Y position range that encompasses a displayed target. Thus, the dwell time can be determined by correlation of position information (e.g., indicating that the cursor is within a bounded target) and velocity information (e.g., indicating that the cursor is either not moving or is moving within the bounded target at a rate that is below a predetermined threshold). It will be appreciated that motor function information can also be acquired concurrently with cognitive data represented by dwell time by computing and analyzing corresponding kinetic information. For example, in PD patients, tremor predominantly occurs when the patient is in a resting condition. That is, when the patient's hand, for example, is purposefully moving, there is little, if any, tremor, while, when the patient's hand is not purposefully moving and is in an essentially resting position, there may be significant tremor, e.g., at a substantially constant 3-8 Hz frequency. Accordingly, the dwell time information may be used as an indicator of which data is significant for measuring tremor in PD patients. For example, the system may determine a measure for tremor front data corresponding to where there was a determined dwell period, in which the user's hand was essentially in a resting position. This concurrent kinetic information can be employed to assess motor function (e.g., the patient could have, some small movements during this time, especially if they have tremor) while cognitive function (e.g., pertaining to information processing and set switching) during this time is also analyzed.

In an example embodiment of the present invention, the system and method may be used to administer and obtain data for certain tests used to measure only motor function, e.g., related to finger tapping or tapping between two points. In an example embodiment of the present invention, the system and method may be used to administer and obtain data for certain tests used to measure only cognitive function, e.g., the Mini Mental State Exam or Raven's Progressive Matrices tests.

FIG. 26 depicts an example of a management GUI 260 that can be utilized to provide access to test data by a user having an appropriate level of authorization. Each set of test data can be associated with a patient via name or other identifying information. As shown in the GUI 260, there can be any number of raw data elements for a given patient, which may generally depend on the test or tests that have been conducted. Each set of raw data, for example, can correspond to a separate set of test data for a given one of the tests or phases (or repetition) of a given test.

FIG. 27 depicts a GUI 270 that can be utilized for managing protocols such as through a management user interface 66 implemented in a system. The protocols management GUI 270 can be utilized, for example, for identifying testing protocols being utilized for a given patient test process. In the example of FIG. 27, the GUI includes selection interface elements 272 that can be utilized to identify protocols set for a patient, such as indicating whether a deep brain stimulator was on or off during the respective tests or the medications and/or dosage thereof administered to the patient at the time of the respective tests. A user, such as a clinician, thus can select a set of protocols associated with a given patient to help understand the effect a given condition has relative to the set of test data acquired for each patient during a given test session.

For instance, these protocols can be implemented and corresponding sets of test data evaluated to ascertain the effects on various conditions such as whether a DBS is on during the test or off as well as whether a patient is on their medication at a prescribed dose or not, and the effect of such a condition on the performance of a test. Those skilled in the art will understand various other protocols and combinations of protocols that can be utilized for specifying patient control parameters associated with a given set of tests.

In view of the foregoing, it will be appreciated that systems and methods have been described that can be implemented to provide a battery of cognitive and motor tests to remotely assess neurological disorders such as neurocognitive and neuromotor disorders such as, for example, PD, Alzheimer's disease, multiple sclerosis, dementia, amyotrophic lateral sclerosis (ALS). Parkinsonian syndrome, trauma-induced brain injury, stroke and multiple systems atrophy (MSA). The systems and methods enable the testing to be performed remotely by a patient-user, and the collection of data in a central data repository, such as to provide access to such information by a clinician and to facilitate further research.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIGS. 1 and 2. Furthermore, portions of the invention may be a computer program product including a hardware computer-readable storage medium having computer readable program code on the medium. Any suitable computer-readable storage medium may be utilized including, but not limited to, static and dynamic storage devices, hard disks, optical storage devices, and magnetic storage devices.

Certain embodiments of the invention have been described herein with reference to block illustrations of methods, systems, and computer program products. It will be that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, when executed by the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 28:
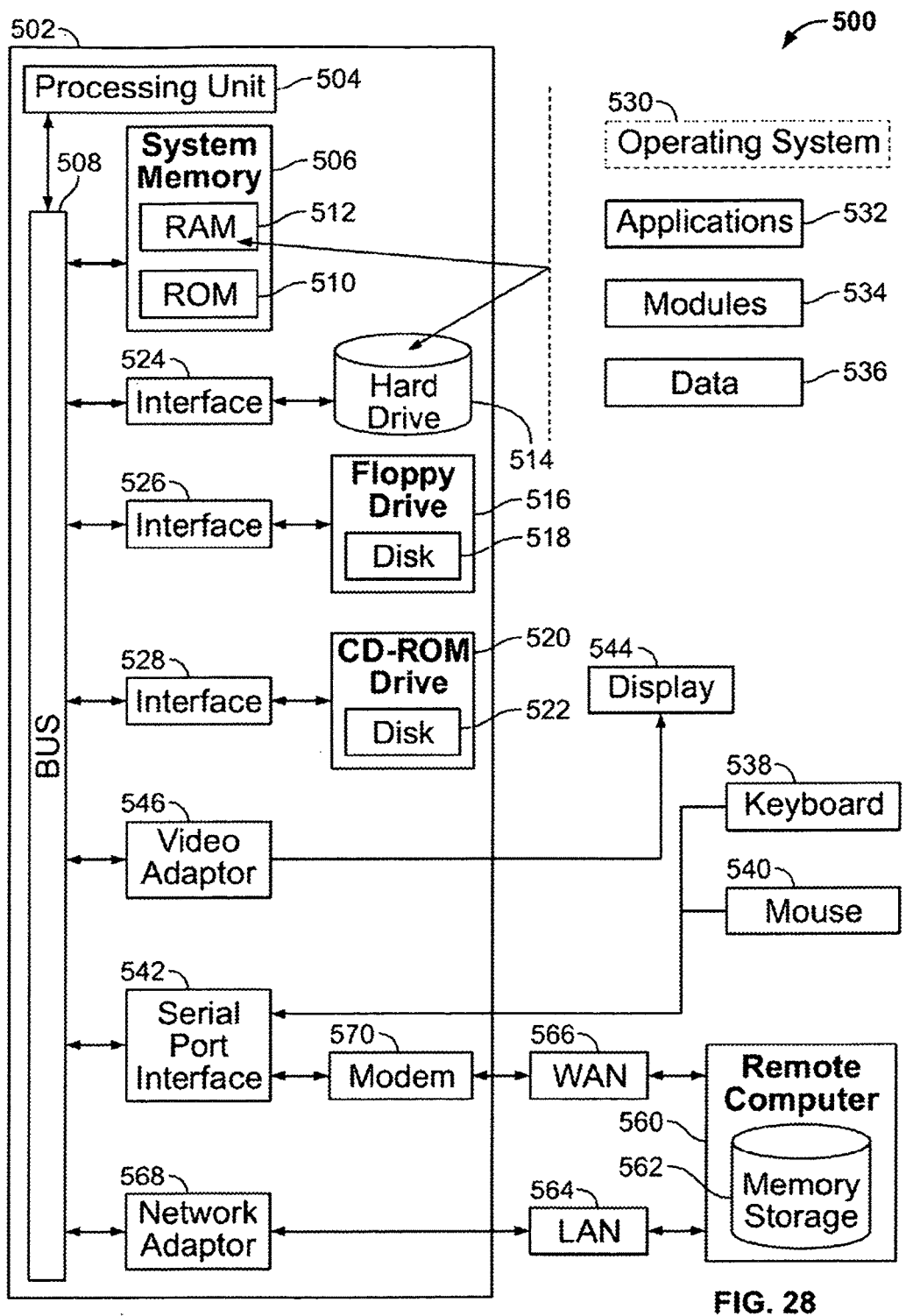
FIG. 28 depicts a computing environment that can be utilized for implementing systems and methods described herein, according to an example embodiment of the present invention.

In this regard, FIG. 28 illustrates one example of a computer system 500 of the type that can be utilized to implement one or more embodiments or the systems and methods described herein for testing and analyzing motor and cognitive function of a patient. The computer system 500 can be implemented on one or more general purpose networked computer systems, embedded computer systems, routers, switches, server devices, client devices, various intermediate devices/nodes and/or stand alone computer systems. Additionally, the computer system 500 or portions thereof can be implemented on various mobile or portable clients such as, for example, a laptop or notebook computer, a personal digital assistant (PDA), and the like.

The system 500 may include a computer 502, which may function, for example, as any of the user devices 54, 56, and 58 and/or the server 52. The computer 502 may include a system bus 508 may include any of several types of bus structures, including, for example, a memory bus or memory controller, a peripheral bus, and a local bus using any of a variety of conventional bus architectures such as peripheral component interconnect (PCI), video electronics standards association (VESA), Microchannel, industry standard architecture (ISA), and extended industry standard architecture (EISA), to name a few. The system memory 506 may include read only memory (ROM) 510 and/or random access memory (RAM) 512. A basic input/output system (BIOS), containing the basic routines that help to transfer information between elements within the computer 502, such as during start-up, may be stored in ROM 510.

The computer 502 also may include, for example, a hard disk drive 514, a magnetic disk drive 516 (e.g., a floppy drive), e.g., to read from or write to a removable disk 518, and an optical disk drive 520 (e.g., a CD-ROM drive), e.g., for reading from or writing to a CD-ROM disk 522 or other optical media. The hard disk drive 514, magnetic disk drive 516, and optical disk drive 520 are connected to the system bus 508 by a hard disk drive interface 524, a magnetic disk drive interface 526, and an optical disk drive interface 528, respectively. The drives and their associated computer-readable media provide nonvolatile storage of data, data structures, computer-executable instructions, etc. for the computer 502. Although, the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment 500, and further that any such media may contain computer-executable instructions for performing the methods of the present invention.

A number of program modules may be stored in the drives and RAM 512, including an operating system 530, one or inure application programs 532, other program modules 534, and program data 536. The operating system 530 in the computer 502 could be any suitable operating system or combinations of operating systems. The application programs 532, other program modules 534, and program data 536 can cooperate to provide motor and cognitive testing on a patient computer device, such as shown and described above. Additionally, application programs 532, other program modules 534, and program data 536 can be used for computation of an indication of motor, cognitive or a combination of motor and cognitive functions of a patient based on the testing data, such as shown and described above.

A user may enter commands and information into the computer 502 through one or more user input devices, such as a keyboard 538 and a pointing device (e.g., a mouse 540). Other input devices (not shown) may include a microphone, a joystick, a game pad, a scanner, touch screen, or the like. The mouse or other pointing device can be utilized to perform a point-and-click action, which includes the action of a computer user moving a cursor to a certain location on a screen (point) and then pressing a mouse button, usually the left button (click), or other pointing device. Such point-and-click can be used with any number of input devices varying from mice, touch pads, keyboards, joysticks, scroll buttons, and roller balls. The information associated with such point and click operations can be provided (e.g., to a central server) as part of the test data for each of the respective, tests, such as described herein.

These and other input devices are often connected to a processing unit 504 through a serial port interface 542 that is coupled to the system bus 508, but may be connected by other interfaces, such as a parallel port, a game port or a universal serial bus (USB). A display device 544, such as a monitor, is also connected to the system bus 508 via an interface, such as a video adapter 546. Other display devices, such as speakers, printers, etc. may be provided instead of or in addition to the monitor. Thus, the output representation for a virtual electrode: is not limited to a graphical representation on a display.

The computer 502 may operate in a networked environment using logical connections to one or more remote computers 560. The remote computer 560 may be a workstation, a server computer, a router, a peer device, or other common network node, and typically includes many or all of the elements described relative to the computer 502, although, for purposes of brevity, only a memory storage device 562 is illustrated in FIG. 28. The logical connections depicted in FIG. 28 may include a LAN 564 and/or a WAN 506. Such networking environments are commonplace in offices, enterprise-wide computer networks, intranets, and the Internet.

When used in a LAN networking environment, the computer 502 is connected to the LAN 564 through a network interface or adapter 568. When used in a WAN networking environment the computer 502 typically includes a modem 570, or is connected to a communications server on an associated LAN, or leas another circuitry arrangement for establishing communications over the WAN 566, such as the Internet. The modem 570, which may be internal or external, is connected to the system bus 508 via the serial port interface 542. In a networked environment, program modules depicted relative to the computer 502, or portions thereof, may be stored in the remote memory storage device 562 (and/or locally). It will be appreciated that the network connections shown are exemplary and other arrangements for establishing a communications link between the computers 502 and 560 may be used.

In accordance with the practices of persons skilled in the art of computer programming, the present invention has been described with reference to acts and symbolic representations of operations that are performed by a computer, such as the computer 502 or remote computer 560, unless otherwise indicated. Such acts and operations are sometimes referred to as being computer-executed. It will be appreciated that the acts and symbolically represented operations include the manipulation by the processing unit 504 of electrical signals representing data bits which causes a resulting transformation or reduction of the electrical signal representation, and the maintenance of data bits at memory locations in the memory system (including the system memory 506, hard drive 514, floppy disks 518, CD-ROM 522, and remote memory storage 562) to thereby reconfigure or otherwise alter the computer system's operation, as well as other processing of signals, and/or store data obtained as results of such processing. The memory locations where such data bits are maintained are physical locations that have particular electrical, magnetic, or optical properties corresponding to the data bits.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. For example, the dimensions and configurations of the targets and the types of user-controlled movement task each patient is instructed to perform can vary from the particular examples shown and described herein. Accordingly, the invention is intended to embrace all such alterations, modifications and variations that fall within the scope of the appended claims. In the claims, unless otherwise indicated, the article "a" is to refer to "one or more than one."

What is claimed is:

1. A computer-implemented method, comprising:
    recording, by a processor, respective time information for each of a plurality of positions of a display device that are traced during administration of a test;
    determining, by the processor, at least one of a plurality of speed values or a plurality of velocity values based on the recorded time information, wherein each value in said determined at least one of the plurality of speed values or the plurality of velocity values represents a rate of change in spatial displacement over time;
    determining derivatives of the plurality of velocity values;
    outputting, by the processor, test result information based on said determined at least one of the plurality of speed values or the plurality of velocity values, wherein the test result information is based additionally on the derivatives; and
    changing, by the processor, stimulation parameters for a programmable implantable stimulator based on said determined at least one of the plurality of speed values or the plurality of velocity values; and
    directing, by the processor, the changed stimulation parameters to the programmable implantable stimulator to provide deep brain stimulation therapy responsive to said determined at least one of the plurality of speed values or the plurality of velocity values.

2. The method of claim 1, wherein the test result information includes a score computed based on said determined at least one of the plurality of speed values or the plurality of velocity values.

3. The method of claim 2, further comprising:
    plotting said determined at least one of the plurality of speed values or the plurality of velocity values as a graph curve; and
    comparing at least one slope of the graph curve to at least one slope of a stored curve;
    wherein the score is based on the comparison.

4. The method of claim 1, wherein the derivatives include acceleration values.

5. The method of claim 1, further comprising:
    responsive to the trace of the plurality of positions, recording the plurality of traced positions, wherein each of said at least one of the plurality of speed values or the plurality of velocity values are recorded in association with respective ones of the recorded plurality of traced positions.

6. The method of claim 5, wherein the recorded plurality of traced positions are recorded at a rate of approximately 30 Hz.

7. The method of claim 5, wherein the test result information includes a graph that plots said at least one of the plurality of speed values or the plurality of velocity values against said recorded plurality of traced positions.

8. The method of claim 5, wherein each of the plurality of traced positions is recorded as a respective pair of an abscissa value and an ordinate value, and, for each pair of abscissa and ordinate values, the abscissa and ordinate values are separately associated with respective ones of said determined at least one of the plurality of speed values or the plurality of velocity values.

9. The method of claim 1, wherein the test result information indicates at least one of cognitive ability or motor skill of a user in response to whose movement the plurality of positions are traced.

10. The method of claim 1, wherein:
    the display device is part of a patient terminal;
    the time information is recorded at a server coupled to the patient terminal via a network; and
    the test result information is output at a clinician terminal coupled to the server via the network.

11. The method of claim 10, wherein the network includes the Internet.

12. The method of claim 1, further comprising
    displaying in a display device a first target and a second target;

responsive to user input corresponding to a trace of a plurality of positions in the display device, which, in combination, form a path from the first target to the second target, recording, by a processor, respective time information for each of the plurality of positions; and determining, by the processor, and outputting, information regarding at least one of a cognitive ability or a motor skill of a user based on the recorded time information.

13. The method of claim 12, further comprising, in accordance with at least a portion of said determined information, modifying at least one of a size of the first and second targets or a distance between the first and second targets.

14. The method of claim 12, further comprising, in accordance with said determined information, setting at least one of (a) a size of, or (b) a distance between a pair of, additional displayed targets.

15. The method of claim 12, further comprising, in accordance with a test-performance history of a user, selecting, by the processor, at least one of (a) a size of, or (b) a distance between, targets of a testing user interface; and displaying in a display device the testing user interface including the first and second targets, in accordance with the selected at least one of size or distance.

16. A computer-implemented method, comprising:
recording, by a processor, respective time information for each of a plurality of positions of a display device that are traced during administration of a test;
determining, by the processor, at least one of a plurality of speed values or a plurality of velocity values based on the recorded time information;
outputting, by the processor, test result information based on said determined at least one of the plurality of speed values or the plurality of velocity values; and
changing, by the processor, stimulation parameters for a programmable implantable stimulator based on said determined at least one of the plurality of speed values or the plurality of velocity values;
directing, by the processor, the changed stimulation parameters to the programmable implantable stimulator to provide deep brain stimulation therapy responsive to said determined at least one of the plurality of speed values or the plurality of velocity values; and
generating at least a portion of the test result information by calculating at least one of an average, standard deviation, mean square error, or root mean square error of a difference of (a) said determined at least one of the plurality of speed values or the plurality of velocity values from ideal values, or (b) derivative values of said determined at least one of the plurality of speed values or the plurality of velocity values from ideal derivative values.

17. A computer-implemented method, comprising:
recording, by a processor, respective time information for each of a plurality of positions of a display device that are traced during administration of a test;
determining, by the processor, at least one of a plurality of speed values or a plurality of velocity values based on the recorded time information;
outputting, by the processor, test result information based on said determined at least one of the plurality of speed values or the plurality of velocity values; and
changing, by the processor, stimulation parameters for a programmable implantable stimulator based on said determined at least one of the plurality of speed values or the plurality of velocity values;
directing, by the processor, the changed stimulation parameters to the programmable implantable stimulator to provide deep brain stimulation therapy responsive to said determined at least one of the plurality of speed values or the plurality of velocity values;
recording, by the processor, a first at least one therapy parameter applied to a patient;
recording, by the processor, a first test result for the patient in association with the first at least one therapy parameter; and
for a user input proposed change to the first at least one therapy parameter to obtain a changed at least one therapy parameter:
searching, by the processor, for a set of at least one patient for each of whom (a) the first test result or a respective second test result that deviates from the first test result by less than a threshold amount is recorded in association with the first at least one therapy parameter or a second at least one therapy parameter that deviates from the first at least one therapy parameter by less than a predetermined threshold amount, and (b) a respective test result is recorded in association with the changed at least one therapy parameter or another respective at least one therapy parameter that deviates from the changed at least one therapy parameter by less than a predetermined threshold amount; and
outputting, by the processor, change information (a) indicative of an expected change to the first test result in response to the proposed change to the first at least one therapy parameter, and (b) based on the at least one respective test result recorded for the set of at least one patient in association with said changed at least one therapy parameter or another respective at least one therapy parameter.

18. The method of claim 17, wherein the output change information includes the expected change to the first test result.

19. The method of claim 17, wherein the output change information includes an expected medical condition classification.

20. The method of claim 17, wherein the output change information includes an expected change in a medical condition classification.

\* \* \* \* \*